US005851788A

United States Patent [19]
Fukuda et al.

[11] Patent Number: 5,851,788
[45] Date of Patent: Dec. 22, 1998

[54] NUCLEIC ACID ENCODING A FAMILY OF ACETYL-COENZYME-A TRANSPORTER PROTEINS, AND PRODUCTS RELATED THERETO

[75] Inventors: Minoru Fukuda, San Diego, Calif.; Akiko Kanamori, Tokoyo; Yoshio Hirabayashi, Saitama, both of Japan

[73] Assignee: The Burnham Institute, La Jolla, Calif.

[21] Appl. No.: 791,887

[22] Filed: Jan. 31, 1997

[51] Int. Cl.$^6$ .............................. C12Q 1/02; C12Q 1/68; C12N 5/00; C07H 21/04
[52] U.S. Cl. .............................. 435/29; 435/6; 435/325; 435/69.1; 435/320.1; 435/975; 536/23.5; 536/24.3; 536/24.31; 935/9; 935/66
[58] Field of Search .............................. 435/6, 29, 69.1, 435/320.1, 172.3, 325, 975; 536/23.5, 24.31, 24.33, 24.5; 514/44; 935/9.66

[56] References Cited

U.S. PATENT DOCUMENTS 5,585,479 12/1996 Hoke et al. .............................. 536/24.5

OTHER PUBLICATIONS

CF Bennett (1996) Science 271: 434.
Stratagene Cloning Systems, 1994 catalog, p. 156.
JF Milligan et al (1993) J Med Chem 36: 1923–1937.
P Westermann et al (1989) Biomed Biochim Acta 48: 85–93.
L Hillier et al (1996) WashU–Merck EST Project, Accession No. W24298.
Abeijon et al., "Molecular cloning of the Golgi apparatus uridine diphosphate–N–acetylglucosamine transporter from *Kluyveromyces lactis*", *Proc. Natl. Acad. Sci. USA*, 93:5963–5968 (1996).
Bhakdi et al., "Mechanism of Membrane Damage by Streptolysin–O", *Infection and Immunity*, 47/1:52–60 (1985).
Davies et al., "Site–specific antibodies as probes of the topology and function of the human erythrocyte glucose transporter", *Biochem J.*, 266:799–808 (1990).
Eckhardt et al., "Expression cloning of the Golgi CMP–sialic acid transporter", *Proc. Natl. Acad. Sci. USA*, 93:7572–7576 (1996).
Hucho and Tsetlin, "Structural Biology of Key Nervous System Proteins", *Journal of Neurochemistry*, 66/5: 1781–1792 (1996).
Johnstone and Stallcup, "Altered Expression of the D1.1 Ganglioside in the Cerebellum of the Weaver Mouse", *Journal of Neurochemistry*, 51/5: 1655–1657 (1988).

Kanamori et al., "Diversity of Sialospingolipids with Modification of Sialic Acid by Acetyl Group and Molecular cloning of a cDNA Encoding a Novel Membrane Protein Responsible for Acetylation", Abstract Booklet, International Symposium on Molecular and Cell Biology of Glycoconjugate Expression, (Aug.13, 1996).
Kwon et al., "Cloning of the cDNa for a Na+/myo–Inositol Cotransporter, a hypertonicity Stress Protein", *The Journal of Biological Chemistry*, 267/9: 6297–6301 (1992).
Landschulz et al., "The Leucine Zipper: A Hypothetical Structure Common to a New Class of DNA Binding Proteins", *Science*, 240: 1759–1764 (1988).
Levine et al., "The D1.1 Antigen: A Cell Surface Marker For Germinal Cells of the Central Nervous System", *The Journal of Neuroscience*, 4/3: 820–831 (1984).
Marini et al., "Cloning and expression of the MEP1 gene encoding an ammonium transporter in *Saccharomyces cerevisiae*", *The EMBO Journal*, 13/15:3456–3463 (1994).
Miura et al., "Human UDP–Galactose Translocator: Molecular Cloning of a Complementary DNA That Complements the Genetic Defect of a Mutant Cell Line Deficient in UDP–Galactose Translocator", *J. Biochem*, 120/2: 236–241 (1996).
Nakayama et al., "Expression Cloning of a Human $G_{T3}$ Synthase", *The Journal of Biological Chemistry*, 271/7: 3684–3691 (1996).
Ogura et al., "Cloning and Expression of cDNA for O–Acetylation of GD3 Ganglioside," *Biochemical and Biophysical Research Communication*, 225/3: 932–938 (1996).
Pacholczck et al., "Expression cloning of a cocaine–and antidepressant–sensitive human noradrenaline transporter", *Nature*, 350:350–354 (1991).
Tanaka et al., "Use of Recombinant P–Glycoprotein Fragments to Produce Antibodies to the Multidrug Transporter", *Biochemical and Biophysical Research Communications*, 166/1: 180–186 (1990).
Varki and Diaz, "The Transport and Utilization of Acetyl Coenzyme A by Rat Liver Golgi Vesicles", *The Journal of Biological Chemistry*, 260/11: 6600–6608 (1985).

*Primary Examiner*—Bruce R. Campell
*Attorney, Agent, or Firm*—Campbell & Flores LLP

[57] ABSTRACT

In accordance with the present invention, there are provided isolated mammalian Acetyl-Coenzyme A Transporter (AT) proteins, anti-AT antibodies, therapeutic compositions, and nucleic acids encoding such. Bioassays and therapeutic methods employing invention AT proteins are also provided.

19 Claims, 2 Drawing Sheets

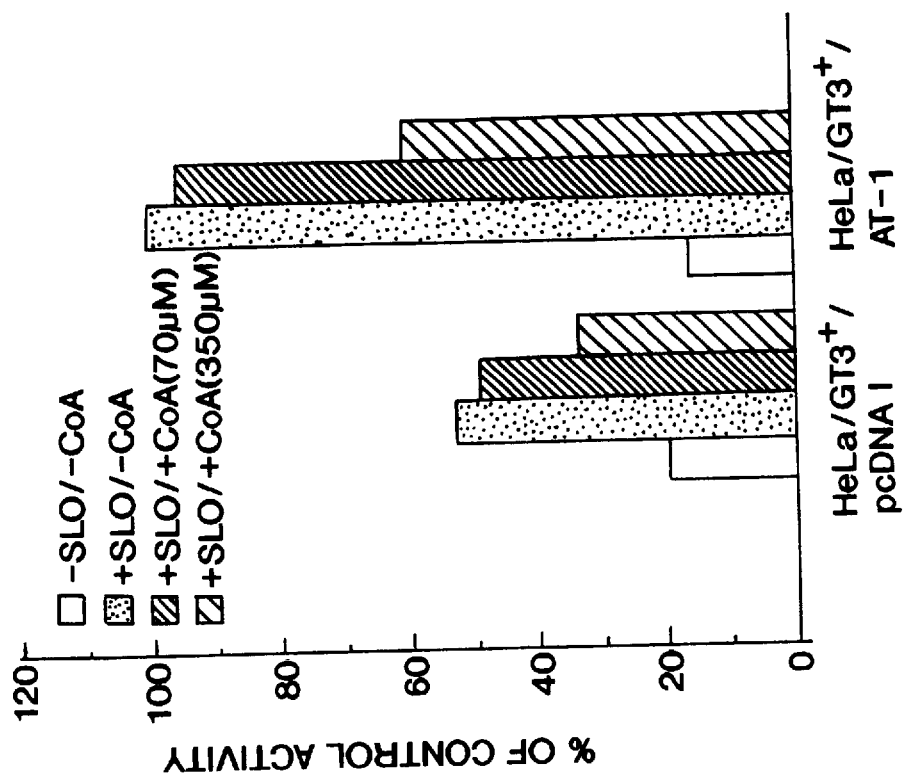
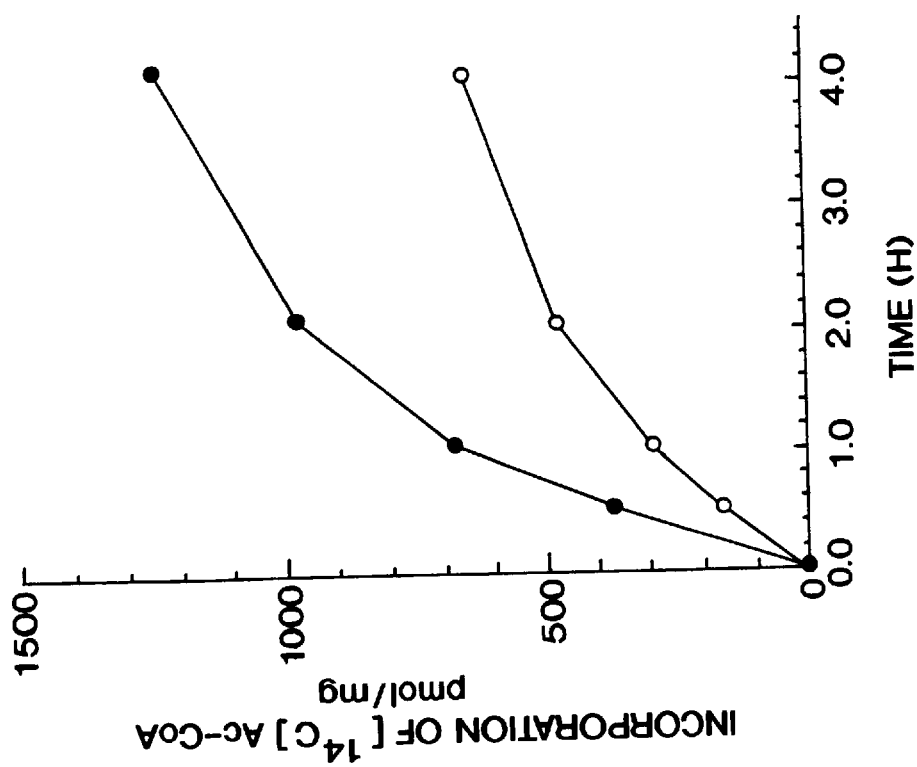

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 2682 base pairs
        ( B ) TYPE: nucleic acid
        ( C ) STRANDEDNESS: both
        ( D ) TOPOLOGY: both ( i i ) MOLECULE TYPE: cDNA ( i x ) FEATURE:
        ( A ) NAME/KEY: CDS
        ( B ) LOCATION: 388..2035

( x i ) SEQUENCE DESCRIPTION: SEQ ID NO:1:

```
GAATTCGCAG CGAGAGCTGG AGGTGTTGGG TCGGGAGACC AGCCATTCGA TCCCGCCGCA        60

GGTAGGAGCT GGTTTCCATC CTGGCACCAC GGCACACACC TCCAGCCTCG AGCCCGGCGC       120

TGCTGCCCGG GGGTCTCCTT CAGGCTCTTT GACGCCGTTC AGGGGGCAC CTATCCAGGC       180

ATCCTCTGGG CCTCTAGCCA GAGGACTGGC TCCCGGCTTC AGCACTCCGG GCTGCAGTAA       240

GAAGTGCCCT TATCGCTCTG AGCCCTGCCA CCATCCCGTG AACCACCGAA ACCCTGGTCC       300

AGCGCGACAG CCTTGGACCT GGGACTGGAC GGATCCAAAA CGCTCAGCCT CGGCCCCCA        360

CAGACGGGGC TCTGCATCGT CTCTGAT ATG TCA CCC ACC ATC TCC CAC AAG            411
                                Met Ser Pro Thr Ile Ser His Lys
                                 1               5
```

```
GAC AGC AGC CGG CAA CGG CGG CCA GGG AAT TTC AGT CAC TCT CTG GAT        459
Asp Ser Ser Arg Gln Arg Arg Pro Gly Asn Phe Ser His Ser Leu Asp
         10                  15                  20

ATG AAG AGC GGT CCC CTG CCG CCA GGC GGT TGG GAT GAC AGT CAT TTG        507
Met Lys Ser Gly Pro Leu Pro Pro Gly Gly Trp Asp Asp Ser His Leu
 25                  30                  35                  40

GAC TCA GCG GGC CGG GAA GGG GAC AGA GAA GCT CTT CTG GGG GAT ACC        555
Asp Ser Ala Gly Arg Glu Gly Asp Arg Glu Ala Leu Leu Gly Asp Thr
                 45                  50                  55

GGC ACT GGC GAC TTC TTA AAA GCC CCA CAG AGC TTC CGG GCC GAA CTA        603
Gly Thr Gly Asp Phe Leu Lys Ala Pro Gln Ser Phe Arg Ala Glu Leu
                 60                  65                  70

AGC AGC ATT TTG CTA CTA CTC TTT CTT TAC GTG CTT CAG GGT ATT CCC        651
Ser Ser Ile Leu Leu Leu Leu Phe Leu Tyr Val Leu Gln Gly Ile Pro
             75                  80                  85

CTG GGC TTG GCG GGA AGC ATC CCA CTC ATT TTG CAA AGC AAA AAT GTT        699
Leu Gly Leu Ala Gly Ser Ile Pro Leu Ile Leu Gln Ser Lys Asn Val
         90                  95                 100

AGC TAT ACA GAC CAA GCT TTC TTC AGT TTT GTC TTT TGG CCC TTC AGT        747
Ser Tyr Thr Asp Gln Ala Phe Phe Ser Phe Val Phe Trp Pro Phe Ser
105                 110                 115                 120

CTC AAA TTA CTC TGG GCC CCG TTG GTT GAT GCG GTC TAC GTT AAG AAC        795
Leu Lys Leu Leu Trp Ala Pro Leu Val Asp Ala Val Tyr Val Lys Asn
                125                 130                 135

TTC GGT CGT CGC AAA TCT TGG CTT GTC CCG ACA CAG TAT ATA CTA GGA        843
Phe Gly Arg Arg Lys Ser Trp Leu Val Pro Thr Gln Tyr Ile Leu Gly
                140                 145                 150

CTC TTC ATG ATC TAT TTA TCC ACT CAG GTG GAC CGT TTG CTT GGG AAT        891
Leu Phe Met Ile Tyr Leu Ser Thr Gln Val Asp Arg Leu Leu Gly Asn
            155                 160                 165

ACC GAT GAC AGA ACA CCC GAC GTG ATT GCT CTC ACT GTG GCG TTC TTT        939
Thr Asp Asp Arg Thr Pro Asp Val Ile Ala Leu Thr Val Ala Phe Phe
        170                 175                 180

TTG TTT GAA TTC TTG GCC GCC ACT CAG GAC ATT GCC GTC GAT GGT TGG        987
Leu Phe Glu Phe Leu Ala Ala Thr Gln Asp Ile Ala Val Asp Gly Trp
185                 190                 195                 200

GCG TTA ACT ATG TTA TCC AGG GAA AAT GTG GGT TAT GCT TCT ACT TGC       1035
Ala Leu Thr Met Leu Ser Arg Glu Asn Val Gly Tyr Ala Ser Thr Cys
                205                 210                 215

AAT TCG GTG GGC CAA ACA GCG GGT TAC TTT TTG GGC AAT GTT TTG TTT       1083
Asn Ser Val Gly Gln Thr Ala Gly Tyr Phe Leu Gly Asn Val Leu Phe
                220                 225                 230

TTG GCC CTT GAA TCT GCC GAC TTT TGT AAC AAA TAT TTG CGG TTT CAG       1131
Leu Ala Leu Glu Ser Ala Asp Phe Cys Asn Lys Tyr Leu Arg Phe Gln
            235                 240                 245

CCT CAA CCC AGA GGA ATC GTT ACT CTT TCA GAT TTC CTT TTT TTC TGG       1179
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| Pro | Gln | Pro | Arg | Gly | Ile | Val | Thr | Leu | Ser | Asp | Phe | Leu | Phe | Phe | Trp |      |
|     | 250 |     |     |     | 255 |     |     |     |     | 260 |     |     |     |     |     |      |

```
GGA ACT GTA TTT TTA ATA ACA ACA ACA TTG GTT GCC CTT CTG AAA AAA    1227
Gly Thr Val Phe Leu Ile Thr Thr Thr Leu Val Ala Leu Leu Lys Lys
265             270                 275                 280

GAA AAC GAA GTA TCA GTA GTA AAA GAA GAA ACA CAA GGG ATC ACA GAT    1275
Glu Asn Glu Val Ser Val Val Lys Glu Glu Thr Gln Gly Ile Thr Asp
                285                 290                 295

ACT TAC AAG CTG CTT TTT GCA ATT ATA AAA ATG CCA GCA GTT CTG ACA    1323
Thr Tyr Lys Leu Leu Phe Ala Ile Ile Lys Met Pro Ala Val Leu Thr
            300             305                 310

TTT TGC CTT CTG ATT CTA ACT GCA AAG ATT GGT TTT TCA GCA GCA GAT    1371
Phe Cys Leu Leu Ile Leu Thr Ala Lys Ile Gly Phe Ser Ala Ala Asp
            315             320                 325

GCT GTA ACA GGA CTG AAA TTG GTA GAA GAG GGA GTA CCC AAA GAA CAT    1419
Ala Val Thr Gly Leu Lys Leu Val Glu Glu Gly Val Pro Lys Glu His
        330             335                 340

TTA GCC TTA TTG GCA GTT CCA ATG GTT CCT TTG CAG ATA ATA CTG CCT    1467
Leu Ala Leu Leu Ala Val Pro Met Val Pro Leu Gln Ile Ile Leu Pro
345             350                 355                 360

CTG ATT ATC AGC AAA TAC ACT GCA GGT CCC CAG CCA TTA AAC ACA TTT    1515
Leu Ile Ile Ser Lys Tyr Thr Ala Gly Pro Gln Pro Leu Asn Thr Phe
                365                 370                 375

TAC AAA GCC ATG CCC TAC AGA TTA TTG CTT GGG TTA GAA TAT GCC CTA    1563
Tyr Lys Ala Met Pro Tyr Arg Leu Leu Leu Gly Leu Glu Tyr Ala Leu
            380             385                 390

CTG GTT TGG TGG ACT CCT AAA GTA GAA CAT CAA GGG GGA TTC CCT ATA    1611
Leu Val Trp Trp Thr Pro Lys Val Glu His Gln Gly Gly Phe Pro Ile
        395             400                 405

TAT TAC TAT ATC GTA GTC CTG CTG AGT TAT GCT TTA CAT CAG GTT ACA    1659
Tyr Tyr Tyr Ile Val Val Leu Leu Ser Tyr Ala Leu His Gln Val Thr
410             415                 420

GTG TAC AGC ATG TAT GTT TCT ATA ATG GCT TTC AAT GCA AAG GTT AGT    1707
Val Tyr Ser Met Tyr Val Ser Ile Met Ala Phe Asn Ala Lys Val Ser
425             430                 435                 440

GAT CCA CTT ATT GGA GGA ACA TAC ATG ACC TTA TTA AAT ACC GTG TCC    1755
Asp Pro Leu Ile Gly Gly Thr Tyr Met Thr Leu Leu Asn Thr Val Ser
                445                 450                 455

AAT CTG GGA GGA AAC TGG CCT TCT ACA GTA GCT CTT TGG CTT GTA GAT    1803
Asn Leu Gly Gly Asn Trp Pro Ser Thr Val Ala Leu Trp Leu Val Asp
            460             465                 470

CCC CTC ACA GTA AAA GAG TGT GTA GGA GCA TCA AAC CAG AAT TGT CGA    1851
Pro Leu Thr Val Lys Glu Cys Val Gly Ala Ser Asn Gln Asn Cys Arg
        475             480                 485

ACA CCT GAT GCT GTT GAG CTT TGC AAA AAA CTG GGT GGC TCA TGT GTT    1899
Thr Pro Asp Ala Val Glu Leu Cys Lys Lys Leu Gly Gly Ser Cys Val
490             495                 500

ACA GCC CTG GAT GGT TAT TAT GTG GAG TCC ATT ATT TGT GTT TTC ATT    1947
Thr Ala Leu Asp Gly Tyr Tyr Val Glu Ser Ile Ile Cys Val Phe Ile
505             510                 515                 520

GGA TTT GGT TGG TGG TTC TTT CTT GGT CCA AAA TTT AAA AAG TTA CAG    1995
Gly Phe Gly Trp Trp Phe Phe Leu Gly Pro Lys Phe Lys Lys Leu Gln
                525                 530                 535

GAT GAA GGA TCA TCT TCG TGG AAA TGC AAA AGG AAC AAT T AATATATATG   2045
Asp Glu Gly Ser Ser Ser Trp Lys Cys Lys Arg Asn Asn
            540             545

CTACTGGACA TTCTAGCAAG GTAATTGTAG TTTAGTTTTA ATTCGGAGAG CAATGATAAT  2105

CAGTGCACAG GAGTATAAAA TATTATTTTA AACAGCGAAA TTAATAATAT AAAATGCCAA  2165

ATGGTTGAAA AAATAGAAAC CTTTCTGTAT ATTTGATCAT ATTTTTTTTT TGCCTTGTCA  2225
```

```
ATGTATTTAA AGTTTACTTA AGGTCAGGAA ATTCTAAAAC AACTTTTCTG GCCTTGTTAT      2285

TTGATGTATA TCTTTTAAAT TTACTGACCA AAGCATGTTT TAAGCTGCAA TGCAGTAGTC      2345

ACGGGTGGTA ACCATGTAGT CAGGTATTGT TATTAGTACC TATCACTGCT GAGCTGTATT      2405

TAAAATTTTG GTACAATATA TAAAATGGAG AAGAGCTTGA TATTCAGGTA CTAACCACAA      2465

CTAGTCTGAC ATTGTTGGCA GTTAAAATCT TATTTTGAAT TGTAAATTAG TTAAATTTTA      2525

TGTGGAATTT GCTGAGAAAA GAATATAGAC TACTGAAATG TCATTTTAGT TATTTTTCTT      2585

ATGACCACAT TGTACAAATG AATCTGTGTT AAAAAGACTA TTTTAAATGT ATTTCCTGCT      2645

TTTGTAAGCA TTAAAGATTT GAATTCCACC ACACTGG                               2682
```

( 2 ) INFORMATION FOR SEQ ID NO:2:

( i ) SEQUENCE CHARACTERISTICS:
        ( A ) LENGTH: 549 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Ser  Pro  Thr  Ile  Ser  His  Lys  Asp  Ser  Ser  Arg  Gln  Arg  Arg  Pro
 1              5                    10                            15

Gly  Asn  Phe  Ser  His  Ser  Leu  Asp  Met  Lys  Ser  Gly  Pro  Leu  Pro  Pro
              20                        25                    30

Gly  Gly  Trp  Asp  Asp  Ser  His  Leu  Asp  Ser  Ala  Gly  Arg  Glu  Gly  Asp
         35                        40                   45

Arg  Glu  Ala  Leu  Leu  Gly  Asp  Thr  Gly  Thr  Gly  Asp  Phe  Leu  Lys  Ala
      50                        55                   60

Pro  Gln  Ser  Phe  Arg  Ala  Glu  Leu  Ser  Ser  Ile  Leu  Leu  Leu  Leu  Phe
 65                  70                        75                             80

Leu  Tyr  Val  Leu  Gln  Gly  Ile  Pro  Leu  Gly  Leu  Ala  Gly  Ser  Ile  Pro
                   85                        90                        95

Leu  Ile  Leu  Gln  Ser  Lys  Asn  Val  Ser  Tyr  Thr  Asp  Gln  Ala  Phe  Phe
               100                      105                      110

Ser  Phe  Val  Phe  Trp  Pro  Phe  Ser  Leu  Lys  Leu  Leu  Trp  Ala  Pro  Leu
              115                      120                      125

Val  Asp  Ala  Val  Tyr  Val  Lys  Asn  Phe  Gly  Arg  Arg  Lys  Ser  Trp  Leu
     130                      135                      140

Val  Pro  Thr  Gln  Tyr  Ile  Leu  Gly  Leu  Phe  Met  Ile  Tyr  Leu  Ser  Thr
145                           150                      155                  160

Gln  Val  Asp  Arg  Leu  Leu  Gly  Asn  Thr  Asp  Asp  Arg  Thr  Pro  Asp  Val
               165                      170                      175

Ile  Ala  Leu  Thr  Val  Ala  Phe  Phe  Leu  Phe  Glu  Phe  Leu  Ala  Ala  Thr
              180                      185                      190

Gln  Asp  Ile  Ala  Val  Asp  Gly  Trp  Ala  Leu  Thr  Met  Leu  Ser  Arg  Glu
              195                      200                      205

Asn  Val  Gly  Tyr  Ala  Ser  Thr  Cys  Asn  Ser  Val  Gly  Gln  Thr  Ala  Gly
     210                      215                      220

Tyr  Phe  Leu  Gly  Asn  Val  Leu  Phe  Leu  Ala  Leu  Glu  Ser  Ala  Asp  Phe
225                      230                      235                      240

Cys  Asn  Lys  Tyr  Leu  Arg  Phe  Gln  Pro  Gln  Pro  Arg  Gly  Ile  Val  Thr
                   245                      250                      255

Leu  Ser  Asp  Phe  Leu  Phe  Phe  Trp  Gly  Thr  Val  Phe  Leu  Ile  Thr  Thr
              260                      265                      270
```

| | | | | | | | | | | | | | | |
|---|---|---|---|---|---|---|---|---|---|---|---|---|---|---|
| Thr | Leu | Val 275 | Ala | Leu | Leu | Lys | Lys 280 | Glu | Asn | Glu | Val | Ser 285 | Val | Val | Lys |
| Glu | Glu 290 | Thr | Gln | Gly | Ile | Thr 295 | Asp | Thr | Tyr | Lys | Leu 300 | Leu | Phe | Ala | Ile |
| Ile 305 | Lys | Met | Pro | Ala | Val 310 | Leu | Thr | Phe | Cys | Leu 315 | Leu | Ile | Leu | Thr | Ala 320 |
| Lys | Ile | Gly | Phe | Ser 325 | Ala | Ala | Asp | Ala | Val 330 | Thr | Gly | Leu | Lys | Leu 335 | Val |
| Glu | Glu | Gly | Val 340 | Pro | Lys | Glu | His | Leu 345 | Ala | Leu | Leu | Ala | Val 350 | Pro | Met |
| Val | Pro | Leu 355 | Gln | Ile | Ile | Leu | Pro 360 | Leu | Ile | Ile | Ser | Lys 365 | Tyr | Thr | Ala |
| Gly | Pro 370 | Gln | Pro | Leu | Asn | Thr 375 | Phe | Tyr | Lys | Ala | Met 380 | Pro | Tyr | Arg | Leu |
| Leu 385 | Leu | Gly | Leu | Glu | Tyr 390 | Ala | Leu | Leu | Val | Trp 395 | Trp | Thr | Pro | Lys | Val 400 |
| Glu | His | Gln | Gly | Gly 405 | Phe | Pro | Ile | Tyr | Tyr 410 | Tyr | Ile | Val | Val | Leu 415 | Leu |
| Ser | Tyr | Ala | Leu 420 | His | Gln | Val | Thr | Val 425 | Tyr | Ser | Met | Tyr | Val 430 | Ser | Ile |
| Met | Ala | Phe 435 | Asn | Ala | Lys | Val | Ser 440 | Asp | Pro | Leu | Ile | Gly 445 | Gly | Thr | Tyr |
| Met | Thr 450 | Leu | Leu | Asn | Thr | Val 455 | Ser | Asn | Leu | Gly | Gly 460 | Asn | Trp | Pro | Ser |
| Thr 465 | Val | Ala | Leu | Trp | Leu 470 | Val | Asp | Pro | Leu | Thr 475 | Val | Lys | Glu | Cys | Val 480 |
| Gly | Ala | Ser | Asn | Gln 485 | Asn | Cys | Arg | Thr | Pro 490 | Asp | Ala | Val | Glu | Leu 495 | Cys |
| Lys | Lys | Leu | Gly 500 | Gly | Ser | Cys | Val | Thr 505 | Ala | Leu | Asp | Gly | Tyr 510 | Tyr | Val |
| Glu | Ser | Ile 515 | Ile | Cys | Val | Phe | Ile 520 | Gly | Phe | Gly | Trp | Trp 525 | Phe | Phe | Leu |
| Gly | Pro 530 | Lys | Phe | Lys | Lys | Leu 535 | Gln | Asp | Glu | Gly | Ser 540 | Ser | Ser | Trp | Lys |
| Cys 545 | Lys | Arg | Asn | Asn | | | | | | | | | | | |

NUCLEIC ACID ENCODING A FAMILY OF ACETYL-COENZYME-A TRANSPORTER PROTEINS, AND PRODUCTS RELATED THERETO This invention was made with government support under grant number R01 CA 48737 and P01 CA 71932 awarded by the National Cancer Institute of the National Institutes. The government has certain rights in the invention.

FIELD OF THE INVENTION

The present invention relates generally to molecular biology and enzymology and more specifically to nucleic acids encoding transporter proteins that regulate the transport of acetyl-coenzyme A (Ac-CoA) across membranes.

BACKGROUND INFORMATION

The structural diversity and complexity of sugar chains in membrane gangliosides are caused in part by the occurrence of several different species of sialic acid molecules. While N-acetylneuraminic acid and N-glycolylneuraminic acid are the most prevalent sialic acids in gangliosides in the brain, their O-acetylated forms are also found as minor components in LD1, B-series gangliosides including GD3 and GT1b, and C-series (NeuAca2-8NeuAca2-8NeuAca2-3Gal-R) gangliosides. Some biological properties are assumed to be associated with the modification of sialic acids by O-acetylation. For example, the expression of 9-O-acetylated gangliosides is apparently associated with neural cell differentiation and migration (Stallcup et al., *Cold Spring Harbor Symp. Ouant. Biol.*, 48:761–773 (1983)). 9-O-acetylated GD3 detected by D1.1 antibody in rat brain was found to be localized in germinal cell zones but to disappear from postmitotic cells. It is absent in normal adult brain (Levine et al., *J. Neuros.*, 4:820–831 (1984)). In the weaver mouse, however, the persistent expression of 9-O-acetylated gangliosides in the adult brain was associated with a defect in cerebellar granule cell migration (Johnstone et al., *J. Neurochem.*, 51:1655–1657 (1988)). The attachment of an O-acetyl group in sialic acid residues causes significant effects on the enzymes of sialic acid metabolism such as sialidases. Effects are also seen on virus binding, cell adhesion, and the immunogenicity of sialic acid residues of gangliosides (for review, see Varki, *Glycobiology*, 2:25–40 (1992)).

In spite of its importance, the O-acetylation mechanism is poorly understood at the molecular and genetic levels. A series of work done by Varki's group indicates that production of O-acetylated gangliosides is not a simple process, requiring the co-localization of the acceptor ganglioside GD3, acetyl-CoA (Ac-CoA) transporter, and acetyltransferase in the same Golgi compartment (Varki, *Glycobiology*, 2:25–40 (1992)). In fact, it was shown that detection of in vitro acetyltransferase activity was extremely difficult and the transfer activity was quickly lost, once intact cell membrane preparations were treated with detergents (Varki and Diaz, *J. Biol. Chem.*, 260:6600–6608 (1985)).

Thus, a need exists to isolate and characterize other protein factors involved in the formation of O-acetylated gangliosides. The present invention satisfies this need and provides related advantages as well.

SUMMARY OF THE INVENTION

In accordance with the present invention, there are provided isolated mammalian Acetyl-Coenzyme A Transporter (AT) proteins. These AT proteins, or fragments thereof, are useful as immunogens for producing anti-AT antibodies, or in therapeutic compositions containing such proteins and/or antibodies. Invention AT proteins are also useful in bioassays to identify agonists and antagonists thereto.

In accordance with the present invention, there are also provided isolated nucleic acids encoding novel AT proteins. Further provided are vectors containing invention nucleic acids, probes that hybridize thereto, host cells transformed therewith, antisense oligonucleotides thereto and related compositions. The nucleic acid molecules described herein can be incorporated into a variety of recombinant expression systems known to those of skill in the art to readily produce isolated recombinant AT proteins. In addition, the nucleic acid molecules of the present invention are useful as probes for assaying for the presence and/or amount of an AT gene or mRNA transcript in a given sample. The nucleic acid molecules described herein, and oligonucleotide fragments thereof, are also useful as primers and/or templates in a PCR reaction for amplifying nucleic acids encoding AT proteins. Also provided are transgenic non-human mammals that express the invention protein.

Antibodies that are immunoreactive with invention AT proteins are also provided. These antibodies are useful in diagnostic assays to determine levels of AT proteins present in a given sample, e.g., tissue samples, Western blots, and the like. The antibodies can also be used to purify AT proteins from crude cell extracts and the like. Moreover, these antibodies are considered therapeutically useful to modulate the biological effect of AT proteins in vivo Methods and diagnostic systems for determining the levels of AT protein in various tissue samples are also provided. These diagnostic methods can be used for monitoring the level of therapeutically administered AT protein or fragments thereof to facilitate the maintenance of therapeutically effective amounts. These diagnostic methods can also be used to diagnose physiological disorders that result from abnormal levels or abnormal structures of the AT protein.

BRIEF DESCRIPTION OF THE DRAWINGS

FIG. 2A illustrates the time dependent incorporation of radioactivity into semi intact cells from [Ac-$^{14}$C]Ac-CoA as described in Example VI. The open circles represent HeLa/GT3+/pcDNAI and the closed ones HeLa/GT3+/AT-1.

FIG. 2B illustrates the effect of CoA on the time dependent incorporation of radioactivity into semi intact cells from [Ac-$^{14}$C]Ac-CoA.

DETAILED DESCRIPTION OF THE INVENTION

Figure 1:
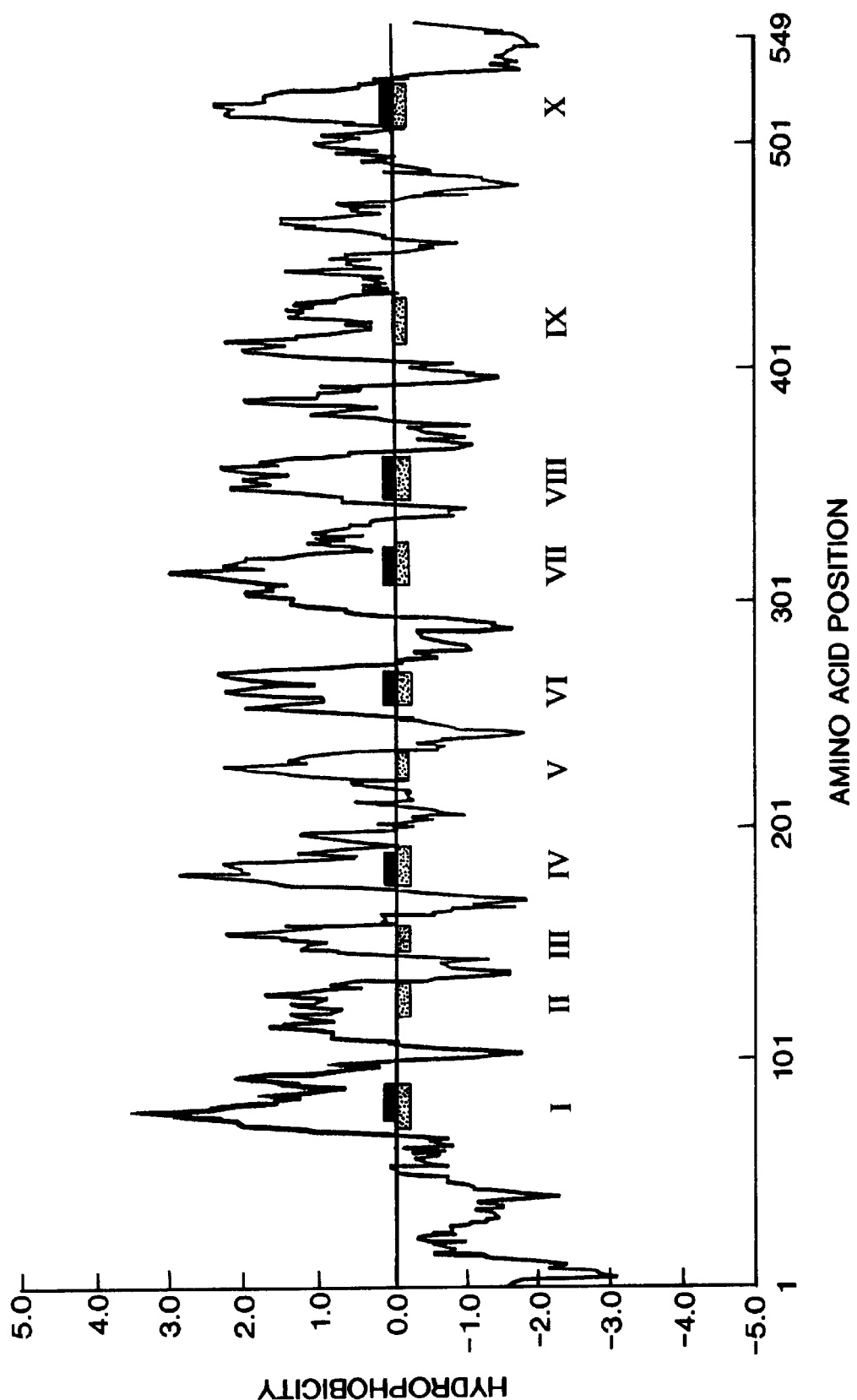
FIG. 1 illustrates a hydropathy plot of SEQ ID NO: 2 (encoding AT-1) analyzed using the method of Kyte and Doolittle with a window size of 10. The shaded and closed boxes denote the transmembrane domains predicted by the Tmpred and Psort programs, respectively.

In accordance with the present invention, there are provided isolated mammalian Acetyl-coenzyme A Transporter (AT) proteins, polypeptides, and fragments thereof encoded by invention nucleic acid. As used herein, the phrase "AT" refers to a mammalian family of isolated and/or substantially pure proteins, preferably human, that are able to transport acetyl-coenzymeA (Ac-CoA) across membranes. Invention AT proteins are further characterized by having the ability to indirectly facilitate the acetylation of sialic acid residues of gangliosides GD3 and GT3. Invention AT proteins include naturally occurring allelic variants thereof encoded by mRNA generated by alternative splicing of a primary transcript, and further including active fragments thereof which retain at least one native biological activity, such as, for example, immunogenicity, and the like.

In another embodiment of the present invention, AT proteins referred to herein, are those polypeptides specifically recognized by an antibody that also specifically recognizes an AT protein (preferably human) including the sequence set forth in SEQ ID NO:2. Invention isolated AT proteins are free of cellular components and/or contaminants normally associated with a native in vivo environment.

The invention proteins are further characterized by being expressed in at least the following cells: heart, brain, placenta, lung, liver, skeletal muscle, kidney and pancreas. The highest level of expression was detected in pancreatic tissues. Two major mRNA transcripts of AT proteins having the sizes 3.3 and 4.3 kb were detected in all tissues examined (observed by a northern blot assay). Two mRNA transcripts of AT proteins having the sizes 2.7 and 3.4 kb were expressed strongly in AT-1 transfected HeLa cells and barely detected in mock transfected HeLa cells. Thus, splice variant cDNA transcripts encoding an AT family of proteins are clearly contemplated by the present invention.

The predicted amino acid sequence of AT-1 (SEQ ID NO:2) has multiple transmembrane spanning domains which are typically observed in many transporters including those for neurotransmitters (for review see Hucho and Tsetlin, *J. Neurochem.*, 66:1781–1792 (1996)), glucose (Davies et al., *Biochem. J.*, 266:799–808 (1990)), ammonia (Marini et al., *EMBO J.*, 12:3456–3463 (1994)), and nucleotide-sugars (Eckhardt et al., *Proc. Natl. Acad. Sci. USA*, 93:7572–7576 (1996); Miura et al., *J. Biochem.*, 120:236–241 (1996); and Abeijon et al., *Proc. Natl. Acad. Sci. USA*, 93:5963–5968 (1996)). Most transporter proteins contain 6 to 12 hydrophobic sequences thought to form membrane spanning α-helices. In the case of the AT-1 protein, the presence of at least 6 transmembrane domains is predicted by Psort analysis.

Moreover, it is important to note that the AT-1 protein contains a leucine zipper motif which was originally found to be involved in dimerization of transcription factors (Landschulz et al., *Science*, 240:1759–1764 (1988)). Very recent studies have shown that the nucleotide-sugar transporter proteins such as those for CMP-NeuAc (Eckhardt et al., *Proc. Natl. Acad. Sci. USA*, 93:7572–7576 (1996)), UDP-Gal (Miura et al., *J. Biochem.*, 120:236–241 (1996)), and UDP-GlcNAc (Abeijon et al., *Proc. Natl. Acad. Sci. USA*, 93:5963–5968 (1996)) also possess this structure, suggesting that these proteins exist as homodimers in the Golgi membrane. Recently, rat liver Golgi PAPS transporter (Mandon et al., *Biochem. Biophy. Res. Commun.*, 225:932–938 (1996)) was also shown to be a homodimer, although it is not known whether the leucine-zipper structure is present in this particular transporter protein. Thus, it is contemplated herein that the AT-1 protein may function as a homodimer having multiple membrane spanning domains. However, the molecular weight of AT-1 protein is substantially larger than those of transporters for CMP-NeuAc, UDP-Gal, and UDP-GlcNAc, suggesting that the AT-1 protein may represent a member of a new AT transporter family.

It has been found that all nucleotide-sugar transporters identified thus far are localized in the Golgi apparatus membrane (Miura et al., *J. Biochem.*, 120:236–241 (1996); Abeijon et al., *Proc. Natl. Acad. Sci. USA*, 93:5963–5968 (1996); and Bhakdi et al., *Infect. Immun.*, 47:52–60 (1985)).

An immunohistochemical study using a specific antibody to AT-1 demonstrated that the AT-1 protein is diffusely present in the cytoplasm, including the endoplasmic reticulum, Golgi, and possibly the mitochondria membranes. This observation indicates that the AT protein family does not function as an acetyltransferase since the acetyltransferase was shown to be enriched in the Golgi membrane (Varki, *Glycobiology*, 2:25–40 (1992) and Varki and Diaz, *J. Biol. Chem.*, 260:6600–6608 (1985)). In addition, the result of in vitro assays using semi intact cells (see, e.g. Example VI, and FIG. 2) indicates that AT-1 is a member of the protein family that functions to transport Ac-CoA across membranes, (e.g., an Ac-CoA transporter).

Homology searches against protein and nucleic acid databases (GenBank, EMBL and Swiss-Prot) were conducted for nucleic and amino acid sequences homologous to the AT-1 nucleic and amino acid sequences set forth in SEQ ID NO:1. Although no significant homologies with known proteins were detected, homology searches identified two putative proteins with high degrees of homology: a putative protein of *S. cerevisiae* [accession nos. Z36088 (EMBL) and P38318 (Swiss Prot)] that has 560 amino acids with 35% amino acid sequence identity; and a protein from *Caenorhabditis elegans* T26C5.3 [EMBL, accession no. Z50859] that has 632 amino acids with 47% amino acid sequence identity. Thus, since it appears that the AT-1 protein is ubiquitous and evolutionarily conserved, and since the occurrence of sialic acid has not been reported in these two organisms, the AT protein family is not likely to function as a sialic acid acetyltransferase. The transcript of AT-1 is more widely distributed than O-acetylated gangliosides, supporting the hypothesis that molecules other than AT-1 protein dictate the regulation of O-acetylated GD3 expression. The results described herein strongly suggest that AT-1 protein functions as an Ac-CoA transporter, and that it may play a key role in acetylation processes other than that of sialic acid in gangliosides.

Use of the terms "isolated" and/or "purified" in the present specification and claims as a modifier of DNA, RNA, polypeptides or proteins means that the DNA, RNA, polypeptides or proteins so designated have been produced in such form by the hand of man, and thus are separated from their native in vivo cellular environment. As a result of this human intervention, the recombinant DNAs, RNAs, polypeptides and proteins of the invention are useful in ways described herein that the DNAs, RNAs, polypeptides or proteins as they naturally occur are not.

As used herein, "mammalian" refers to the variety of species from which invention AT proteins are derived, e.g., human, rat, mouse, rabbit, monkey, baboon, bovine, porcine, ovine, canine, feline, and the like.

Presently preferred AT proteins of the invention include amino acid sequences that are substantially the same as the protein sequence set forth in SEQ ID NO:2, as well as biologically active, modified forms thereof. Those of skill in the art will recognize that numerous residues of the above-described sequences can be substituted with other, chemically, sterically and/or electronically similar residues without substantially altering the biological activity of the resulting protein species. In addition, larger or smaller polypeptide sequences containing substantially the same sequence as SEQ ID NO:2 therein (e.g., splice variants, active fragments of AT, and the like) are contemplated.

As employed herein, the term "substantially the same amino acid sequence" refers to amino acid sequences having at least about 70% identity with respect to the reference amino acid sequence, and retaining comparable functional and biological activity characteristic of the protein defined by the reference amino acid sequence. Preferably, proteins having "substantially the same amino acid sequence" will have at least about 80%, more preferably 90% amino acid identity with respect to the reference amino acid sequence; with greater than about 95% amino acid sequence identity being especially preferred. It is recognized, however, that polypeptides (or nucleic acids referred to hereinbefore) containing less than the described levels of sequence identity arising as splice variants or coat are modified by conservative amino acid substitutions, or by substitution of degenerate codons are also encompassed within the scope of the present invention. A preferred AT protein disclosed herein, is human AT-1 (SEQ ID NO:2).

The term "biologically active" or "functional", when used herein as a modifier of invention AT protein(s), or polypeptide fragment thereof, refers to a polypeptide that exhibits at least one of the functional characteristics attributed to AT. For example, one biological activity of AT is the ability to transport acetyl-coenzymeA (Ac-CoA) across cellular membranes, preferably membranes of intracellular organelles, such as, for example Golgi membranes, endoplasmic reticulum membranes, mitochondria membranes, and the like. Yet another biological activity of AT is the ability to indirectly facilitate the acetylation of sialic acid residues of gangliosides GD3 and GT3.

Another biological activity of AT is the ability to act as an immunogen for the production of polyclonal and monoclonal antibodies that bind specifically to AT. Thus, an invention nucleic acid encoding AT will encode a polypeptide specifically recognized by an antibody that also specifically recognizes the AT protein (preferably human) including the sequence set forth in SEQ ID NO:2 (AT-1). Such activity may be assayed by any method known to those of skill in the art. For example, a test-polypeptide encoded by an AT cDNA can be used to produce antibodies, which are then assayed for their ability to bind to the protein including the sequence set forth in SEQ ID NO:2. If the antibody binds to the test-polypeptide and the protein including the sequence set forth in SEQ ID NO:2 with substantially the same affinity, then the polypeptide possesses the required biological activity.

The invention AT proteins can be isolated by a variety of methods well-known in the art, e.g., the recombinant expression systems described herein, precipitation, gel filtration, ion-exchange, reverse-phase and affinity chromatography, and the like. Other well-known methods are described in Deutscher et al., *Guide to Protein Purification: Methods in Enzymology* Vol. 182, (Academic Press, (1990)), which is incorporated herein by reference. Alternatively, the isolated polypeptides of the present invention can be obtained using well-known recombinant methods as described, for example, in Sambrook et al., (supra., 1989).

An example of the means for preparing the invention polypeptide(s) is to express nucleic acids encoding the AT in a suitable host cell, such as a bacterial cell, a yeast cell, an amphibian cell (i.e., oocyte), or a mammalian cell, using methods well known in the art, and recovering the expressed polypeptide, again using well-known methods. Invention AT polypeptides can be isolated directly from cells that have been transformed with expression vectors as described herein. The invention polypeptide, biologically active fragments, and functional equivalents thereof can also be produced by chemical synthesis. For example, synthetic polypeptides can be produced using Applied Biosystems, Inc. Model 430A or 431A automatic peptide synthesizer (Foster City, Calif.) employing the chemistry provided by the manufacturer.

Also encompassed by the term AT are active fragments or polypeptide analogs thereof. The term "active fragment" refers to a peptide fragment that is a portion of a full length AT protein, provided that the portion has an activity that is characteristic of the corresponding full length protein. For example, an active fragment of an AT protein, such as a cytoplasmic domain can have an activity such as the ability, for example, to bind Ac-CoA or to mediate membrane transport of Ac-CoA after binding to Ac-CoA. The characteristic of an active fragment of an AT protein to elicit an immune response is useful for obtaining an anti-AT antibody. Thus, the invention also provides active fragments of invention AT proteins, which can be identified using the assays described herein.

The term "polypeptide analog" includes any polypeptide having an amino acid residue sequence substantially identical to a sequence specifically shown herein in which one or more residues have been conservatively substituted with a functionally similar residue and which displays the ability to mimic AT as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

As used herein the phrase "conservative substitution" also includes the use of a chemically derivatized residue in place of a non-derivatized residue, provided that such polypeptide displays the required binding activity. The phrase "chemical derivative" refers to a subject polypeptide having one or more residues chemically derivatized by reaction of a functional side group. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides of the present invention also include any polypeptide having one or more additions and/or deletions of residues, relative to the sequence of a polypeptide whose sequence is shown herein, so long as the required activity is maintained.

The present invention also provides compositions containing an acceptable carrier and any of an isolated, purified AT polypeptide, an active fragment or polypeptide analog thereof, or a purified, mature protein and active fragments thereof, alone or in combination with each other. These polypeptides or proteins can be recombinantly derived, chemically synthesized or purified from native sources. As used herein, the term "acceptable carrier" encompasses any of the standard pharmaceutical carriers, such as phosphate buffered saline solution, water and emulsions such as an oil/water or water/oil emulsion, and various types of wetting agents.

In accordance with another embodiment of the present invention, there are provided isolated nucleic acids, which encode invention AT (acetyl-coenzymeA transporter) proteins, and fragments thereof. The nucleic acid molecules described herein are useful for producing invention proteins, when such nucleic acids are incorporated into a variety of protein expression systems known to those of skill in the art. In addition, such nucleic acid molecules or fragments thereof can be labeled with a readily detectable substituent and used as hybridization probes for assaying for the presence and/or amount of an AT gene or mRNA transcript in a given sample. The nucleic acid molecules described herein, and fragments thereof, are also useful as primers and/or templates in a PCR reaction for amplifying genes encoding the invention protein described herein.

The term "nucleic acid" (also referred to as polynucleotides) encompasses ribonucleic acid (RNA) or deoxyribonucleic acid (DNA), probes, oligonucleotides, and primers. DNA can be either complementary DNA (cDNA) or genomic DNA, e.g. a gene encoding an AT protein. One means of isolating a nucleic acid encoding an AT polypeptide is to probe a mammalian genomic library with a natural or artificially designed DNA probe using methods well known in the art. DNA probes derived from the AT gene are particularly useful for this purpose. DNA and cDNA molecules that encode AT polypeptides can be used to obtain complementary genomic DNA, cDNA or RNA from mammalian (e.g., human, mouse, rat, rabbit, pig, and the like), or other animal sources, or to isolate related cDNA or genomic clones by the screening of cDNA or genomic libraries, by methods described in more detail below. Examples of nucleic acids are RNA, cDNA, or isolated genomic DNA encoding an AT polypeptide. Such nucleic acids may include, but are not limited to, nucleic acids having substantially the same nucleotide sequence as set forth in SEQ ID NO:1, at least nucleotides 388–2034 of SEQ ID NO:1, or splice variant cDNA sequences thereof.

As used herein, the phrases "splice variant" or "alternatively spliced", when used to describe a particular nucleotide sequence encoding an invention receptor, refers to a cDNA sequence that results from the well known eukaryotic RNA splicing process. The RNA splicing process involves the removal of introns and the joining of exons from eukaryotic primary RNA transcripts to create mature RNA molecules of the cytoplasm. Methods of isolating splice variant nucleotide sequences are well known in the art. For example, one of skill in the art can employ nucleotide probes derived from the AT encoding cDNA of SEQ ID NO:1 to screen a cDNA or genomic library as described herein.

In one embodiment of the present invention, cDNAs encoding the invention AT proteins disclosed herein include substantially the same nucleotide sequence as set forth in SEQ ID NO:1. In another embodiment of the present invention, cDNA molecules encoding the invention proteins include the same nucleotide sequence as nucleotides 388–2034 of SEQ ID NO:1.

As employed herein, the term "substantially the same nucleotide sequence" refers to DNA having sufficient identity to the reference polynucleotide, such that it will hybridize to the reference nucleotide under moderately stringent hybridization conditions. In one embodiment, DNA having substantially the same nucleotide sequence as the reference nucleotide sequence encodes substantially the same amino acid sequence as that set forth in SEQ ID NO:2, or a larger amino acid sequence including SEQ ID NO:2. In another embodiment, DNA having "substantially the same nucleotide sequence" as the reference nucleotide sequence has at least 60% identity with respect to the reference nucleotide sequence. DNA having at least 70%, more preferably at least 90%, yet more preferably at least 95%, identity to the reference nucleotide sequence is preferred.

The present invention also encompasses nucleic acids which differ from the nucleic acids shown in SEQ ID NO:1, but which have the same phenotype. Phenotypically similar nucleic acids are also referred to as "functionally equivalent nucleic acids". As used herein, the phrase "functionally equivalent nucleic acids" encompasses nucleic acids characterized by slight and non-consequential sequence variations that will function in substantially the same manner to produce the same protein product(s) as the nucleic acids disclosed herein. In particular, functionally equivalent nucleic acids encode polypeptides that are the same as those disclosed herein or that have conservative amino acid variations, or that encode larger polypeptides that include SEQ ID NO:2. For example, conservative variations include substitution of a non-polar residue with another non-polar residue, or substitution of a charged residue with a similarly charged residue. These variations include those recognized by skilled artisans as those that do not substantially alter the tertiary structure of the protein.

Further provided are nucleic acids encoding AT polypeptides that, by virtue of the degeneracy of the genetic code, do not necessarily hybridize to the invention nucleic acids under specified hybridization conditions. Preferred nucleic acids encoding the invention AT polypeptide are comprised of nucleotides that encode substantially the same amino acid sequence set forth in SEQ ID NO:2 (i.e., AT-1).

Thus, an exemplary nucleic acid encoding an invention AT protein may be selected from:
  (a) DNA encoding the amino acid sequence set forth in SEQ ID NO:2;
  (b) DNA that hybridizes to the DNA of (a) under moderately stringent conditions, wherein said DNA encodes biologically active AT; or
  (c) DNA degenerate with respect to either (a) or (b) above, wherein said DNA encodes biologically active AT.

Hybridization refers to the binding of complementary strands of nucleic acid (i.e., sense:antisense strands or probe:target-DNA) to each other through hydrogen bonds, similar to the bonds that naturally occur in chromosomal DNA. Stringency levels used to hybridize a given probe with target-DNA can be readily varied by those of skill in the art.

The phrase "stringent hybridization" is used herein to refer to conditions under which polynucleic acid hybrids are stable. As known to those of skill in the art, the stability of hybrids is reflected in the melting temperature ($T_m$) of the hybrids. In general, the stability of a hybrid is a function of sodium ion concentration and temperature. Typically, the hybridization reaction is performed under conditions of lower stringency, followed by washes of varying, but higher, stringency. Reference to hybridization stringency relates to such washing conditions.

As used herein, the phrase "moderately stringent hybridization" refers to conditions that permit target-DNA to bind a complementary nucleic acid that has about 60% identity, preferably about 75% identity, more preferably about 85% identity to the target DNA; with greater than about 90% identity to target-DNA being especially preferred. Preferably, moderately stringent conditions are conditions equivalent to hybridization in 50% formamide, 5×Denhart's solution, 5×SSPE, 0.2% SDS at 42° C., followed by washing in 0.5×SSPE, 0.2% SDS, at 42° C.

The phrase "high stringency hybridization" refers to conditions that permit hybridization of only those nucleic acid sequences that form stable hybrids in 0.018M NaCl at 65° C. (i.e., if a hybrid is not stable in 0.018M NaCl at 65° C., it will not be stable under high stringency conditions, as contemplated herein). High stringency conditions can be provided, for example, by hybridization in 50% formamide, 5×Denhart's solution, 5×SSPE, 0.2% SDS at 42° C., followed by washing in 0.1×SSPE, and 0.1% SDS at 65° C.

The phrase "low stringency hybridization" refers to conditions equivalent to hybridization in 10% formamide, 5×Denhart's solution, 6×SSPE, 0.2% SDS at 37° C., followed by washing in 1×SSPE, 0.2% SDS, at 50° C. Denhart's solution and SSPE (see, e.g., Sambrook et al., *Molecular Cloning, A Laboratory Manual*, Cold Spring Harbor Laboratory Press, 1989) are well known to those of skill in the art as are other suitable hybridization buffers.

As used herein, the term "degenerate" refers to codons that differ in at least one nucleotide from a reference nucleic acid, e.g., SEQ ID NO:1, but encode the same amino acids as the reference nucleic acid. For example, codons specified by the triplets "UCU", "UCC", "UCA", and "UCG" are degenerate with respect to each other since all four of these codons encode the amino acid serine.

Preferred nucleic acids encoding the invention polypeptide(s) hybridize under moderately stringent, preferably high stringency, conditions to substantially the entire sequence of the nucleic acid sequence set forth in SEQ ID NO: 1.

Site-directed mutagenesis of any region of AT cDNA is contemplated herein for the production of mutant AT cDNAs. For example, the Transformer Mutagenesis Kit (available from Clontech) can be used to construct a variety of missense and/or nonsense mutations to AT cDNA, and the like.

The invention nucleic acids can be produced by a variety of methods well-known in the art, e.g., the methods described herein, employing PCR amplification using oligonucleotide primers from various regions of SEQ ID NO:1, and the like.

In accordance with a further embodiment of the present invention, optionally labeled AT-encoding cDNAs, or fragments thereof, can be employed to probe library(ies) (e.g., cDNA, genomic, and the like) for additional nucleic acid sequences encoding related novel mammalian AT proteins. Construction of mammalian cDNA and genomic libraries, preferably a human library, is well-known in the art. Screening of such a cDNA or genomic library is initially carried out under low-stringency conditions, which comprise a temperature of less than about 42° C., a formamide concentration of less than about 50%, and a moderate to low salt concentration.

In one embodiment, probe-based screening conditions comprise a temperature of about 37° C., a formamide concentration of about 20%, and a salt concentration of about 5× standard saline citrate (SSC; 20×SSC contains 3M sodium chloride, 0.3M sodium citrate, pH 7.0). Such conditions will allow the identification of sequences which have a substantial degree of similarity with the probe sequence, without requiring perfect homology. The phrase "substantial similarity" refers to sequences which share at least 50% homology. Preferably, hybridization conditions will be selected which allow the identification of sequences having at least 70% homology with the probe, while discriminating against sequences which have a lower degree of homology with the probe. As a result, nucleic acids having substantially the same (i.e., similar) nucleotide sequence as nucleotides 388–2034 of SEQ ID NO:1 are obtained.

As used herein, a nucleic acid "oligonucleotide", also referred to herein as a probe or primer, is single-stranded DNA or RNA, or analogs thereof, that has a sequence of nucleotides that includes at least 14, preferably at least 20, more preferably at least 50, contiguous bases that are the same as (or the complement of) any 14 or more contiguous bases set forth in any of SEQ ID NO: 1. Preferred regions from which to construct probes include 5' and/or 3' coding regions of SEQ ID NO:1. In addition, the entire cDNA encoding region of an invention AT protein, or the entire sequence corresponding to SEQ ID NO:1 (AT), may be used as a probe. Probes may be labeled by methods well-known in the art, as described hereinafter, and used in various diagnostic kits.

As used herein, the terms "label" and "indicating means" in their various grammatical forms refer to single atoms and molecules that are either directly or indirectly involved in the production of a detectable signal. Any label or indicating means can be linked to invention nucleic acid probes, expressed proteins, polypeptide fragments, or antibody molecules. These atoms or molecules can be used alone or in conjunction with additional reagents. Such labels are themselves well-known in clinical diagnostic chemistry.

The labeling means can be a fluorescent labeling agent that chemically binds to antibodies or antigens without denaturation to form a fluorochrome (dye) that is a useful immunofluorescent tracer. A description of immunofluorescent analytic techniques is found in DeLuca, "Immunofluorescence Analysis", in *Antibody As a Tool*, Marchalonis et al., eds., John Wiley & Sons, Ltd., pp. 189–231 (1982), which is incorporated herein by reference.

In one embodiment, the indicating group is an enzyme, such as horseradish peroxidase (HRP), glucose oxidase, and the like. In another embodiment, radioactive elements are employed labeling agents. The linking of a label to a substrate, i.e., labeling of nucleic acid probes, antibodies, polypeptides, and proteins, is well known in the art. For instance, an invention antibody can be labeled by metabolic incorporation of radiolabeled amino acids provided in the culture medium. See, for example, Galfre et al., *Meth. Enzymol.*, 73:3–46 (1981). Conventional means of protein conjugation or coupling by activated functional groups are particularly applicable. See, for example, Aurameas et al., *Scand. J. Immunol.*, Vol. 8, Suppl. 7:7–23 (1978), Rodwell et al., *Biotech.*, 3:889–894 (1984), and U.S. Pat. No. 4,493, 795.

Also provided are antisense oligonucleotides having a sequence capable of binding specifically with any portion of an mRNA that encodes AT polypeptides so as to prevent translation of the mRNA. The antisense oligonucleotide may have a sequence capable of binding specifically with any portion of the sequence of the cDNA encoding AT polypeptides. As used herein, the phrase "binding specifically" encompasses the ability of a nucleic acid sequence to recognize a complementary nucleic acid sequence and to form double-helical segments therewith via the formation of hydrogen bonds between the complementary base pairs. An example of an antisense oligonucleotide is an antisense oligonucleotide comprising chemical analogs of nucleotides.

Compositions comprising an amount of the antisense oligonucleotide, described above, effective to reduce expression of AT polypeptides by passing through a cell membrane and binding specifically with mRNA encoding AT polypeptides so as to prevent translation and an acceptable hydrophobic carrier capable of passing through a cell membrane are also provided herein. Suitable hydrophobic carriers are described, for example, in U.S. Pat. Nos. 5,334,761; 4,889,953; 4,897,355, and the like. The acceptable hydrophobic carrier capable of passing through cell membranes may also comprise a structure which binds to a receptor specific for a selected cell type and is thereby taken up by cells of the selected cell type. The structure may be part of a protein known to bind to a cell-type specific receptor.

Antisense oligonucleotide compositions are useful to inhibit translation of mRNA encoding invention polypeptides. Synthetic oligonucleotides, or other antisense chemical structures are designed to bind to mRNA encoding AT polypeptides and inhibit translation of mRNA and are useful as compositions to inhibit expression of AT associated genes in a tissue sample or in a subject.

In accordance with another embodiment of the invention, kits are provided for detecting the presence of an AT nucleic sequence comprising at least one oligonucleotide, e.g., a probe or antisense oligonucleotide, according to the present invention. Such kits can be used for detecting mutations, duplications, deletions, rearrangements or aneuploidies in an AT gene.

The present invention provides means to modulate levels of expression of AT polypeptides by employing synthetic antisense oligonucleotide compositions (hereinafter SAOC) which inhibit translation of mRNA encoding these polypeptides. Synthetic oligonucleotides, or other antisense chemical structures designed to recognize and selectively bind to mRNA, are constructed to be complementary to portions of the AT coding strand or nucleotide sequences shown in SEQ ID NO:1. The SAOC is designed to be stable in the blood stream for administration to a subject by injection or by direct tumor site integration, or stable in laboratory cell culture conditions. The SAOC is designed to be capable of passing through the cell membrane in order to enter the cytoplasm of the cell by virtue of physical and chemical properties of the SAOC which render it capable of passing through cell membranes, for example, by designing small, hydrophobic SAOC chemical structures, or by virtue of specific transport systems in the cell which recognize and transport the SAOC into the cell. In addition, the SAOC can be designed for administration only to certain selected cell populations by targeting the SAOC to be recognized by specific cellular uptake mechanisms which bind and take up the SAOC only within select cell populations.

For example, the SAOC may be designed to bind to a receptor found only in a certain cell type, as discussed supra. The SAOC is also designed to recognize and selectively bind to target mRNA sequence, which may correspond to a sequence contained within the sequence shown in SEQ ID NO:1. The SAOC is designed to inactivate target mRNA sequence by either binding thereto and inducing degradation of the mRNA by, for example, RNase I digestion, or inhibiting translation of mRNA target sequence by interfering with the binding of translation-regulating factors or ribosomes, or inclusion of other chemical structures, such as ribozyme sequences or reactive chemical groups which either degrade or chemically modify the target mRNA. SAOCs have been shown to be capable of such properties when directed against mRNA targets (see Cohen et al., *TIPS*, 10:435 (1989) and Weintraub, *Sci. American*, January (1990), p.40; both incorporated herein by reference).

In accordance with yet another embodiment of the present invention, there is provided a method for the recombinant production of invention AT protein(s) by expressing the above-described nucleic acid sequences in suitable host cells. Recombinant DNA expression systems that are suitable to produce AT proteins described herein are well-known in the art. For example, the above-described nucleotide sequences can be incorporated into vectors for further manipulation. As used herein, vector (or plasmid) refers to discrete elements that are used to introduce heterologous DNA into cells for either expression or replication thereof.

Suitable expression vectors are well-known in the art, and include vectors capable of expressing DNA operatively linked to a regulatory sequence, such as a promoter region that is capable of regulating expression of such DNA. Thus, an expression vector refers to a recombinant DNA or RNA construct, such as a plasmid, a phage, recombinant virus or other vector that, upon introduction into an appropriate host cell, results in expression of the inserted DNA. Appropriate expression vectors are well known to those of skill in the art and include those that are replicable in eukaryotic cells and/or prokaryotic cells and those that remain episomal or those which integrate into the host cell genome. In addition, vectors may contain appropriate packaging signals that enable the vector to be packaged by a number of viral virions, e.g., retroviruses, herpes viruses, adenoviruses, resulting in the formation of a "viral vector."

As used herein, a promoter region refers to a segment of DNA that controls transcription of DNA to which it is operatively linked. The promoter region includes specific sequences that are sufficient for RNA polymerase recognition, binding and transcription initiation. In addition, the promoter region includes sequences that modulate this recognition, binding and transcription initiation activity of RNA polymerase. These sequences may be cis acting or may be responsive to trans acting factors. Promoters, depending upon the nature of the regulation, may be constitutive or regulated. Exemplary promoters contemplated for use in the practice of the present invention include the SV40 early promoter, the cytomegalovirus (CMV) promoter, the mouse mammary tumor virus (MMTV) steroid-inducible promoter, Moloney murine leukemia virus (MMLV) promoter, and the like.

As used herein, the term "operatively linked" refers to the functional relationship of DNA with regulatory and effector nucleotide sequences, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA.

As used herein, expression refers to the process by which polynucleic acids are transcribed into mRNA and translated into peptides, polypeptides, or proteins. If the polynucleic acid is derived from genomic DNA, expression may, if an appropriate eukaryotic host cell or organism is selected, include splicing of the mRNA.

Prokaryotic transformation vectors are well-known in the art and include pBluescript and phage Lambda ZAP vectors (Stratagene, La Jolla, Calif.), and the like. Other suitable vectors and promoters are disclosed in detail in U.S. Pat. No. 4,798,885, issued January 17, 1989, the disclosure of which is incorporated herein by reference in its entirety.

Other suitable vectors for transformation of *E. coli* cells include the pET expression vectors (Novagen, see U.S. Pat. No. 4,952,496), e.g., pET11a, which contains the T7 promoter, T7 terminator, the inducible *E. coli* lac operator, and the lac repressor gene; and pET 12a–c, which contain the T7 promoter, T7 terminator, and the *E. coli* ompT secretion signal. Another suitable vector is the pIN-IIIompA2 (see Duffaud et al., *Meth. in Enzymology*, 153:492–507, 1987), which contains the lpp promoter, the lacUV5 promoter operator, the ompA secretion signal, and the lac repressor gene.

Exemplary, eukaryotic transformation vectors, include the cloned bovine papilloma virus genome, the cloned genomes of the murine retroviruses, and eukaryotic cassettes, such as the pSV-2 gpt system (described by Mulligan and Berg, *Nature*, 277:108–114 (1979)) the Okayama-Berg cloning system (*Mol. Cell Biol.*, 2:161–170, (1982)), and the expression cloning vector described by Genetics Institute (*Science*. 228:810–815 (1985)), are available which provide substantial assurance of at least some expression of the protein of interest in the transformed eukaryotic cell line.

Particularly preferred base vectors which contain regulatory elements that can be linked to the invention AT-encoding DNAs for transfection of mammalian cells are cytomegalovirus (CMV) promoter-based vectors such as pcDNA1 (Invitrogen, San Diego, Calif.), MMTV promoter-based vectors such as pMAMNeo (Clontech, Palo Alto, Calif.) and pMSG (Pharmacia, Piscataway, N.J.), and SV40 promoter-based vectors such as pSVβ ((Clontech, Palo Alto, Calif.).

In accordance with another embodiment of the present invention, there are provided "recombinant cells" containing the nucleic acid molecules (i.e., DNA or mRNA) of the present invention. Methods of transforming suitable host cells, preferably bacterial cells, and more preferably *E. coli* cells, as well as methods applicable for culturing said cells containing a gene encoding a heterologous protein, are generally known in the art. See, for example, Sambrook et al., *Molecular Cloning*: A Laboratory Manual (2 ed.), Cold Spring Harbor Laboratory Press, Cold Spring Harbor, N.Y., USA (1989).

Exemplary methods of introducing (transducing) expression vectors containing invention nucleic acids into host cells to produce transduced recombinant cells (i.e., cells containing recombinant heterologous nucleic acid) are well-known in the art (see, for review, Friedmann, *Science*, 244:1275–1281 (1989); Mulligan, *Science*, 260:926–932 (1993), each of which are incorporated herein by reference in their entirety). Exemplary methods of transduction include, e.g., infection employing viral vectors (see, e.g., U.S. Pat. No. 4,405,712 and 4,650,764), calcium phosphate transfection (U.S. Pat. Nos. 4,399,216 and 4,634,665), dextran sulfate transfection, electroporation, lipofection (see, e.g., U.S. Pat. Nos. 4,394,448 and 4,619,794), cytofection, particle bead bombardment, and the like. The heterologous nucleic acid can optionally include sequences which allow for its extrachromosomal (i.e., episomal) maintenance, or the heterologous DNA can be caused to integrate into the genome of the host (as an alternative means to ensure stable maintenance in the host).

Host organisms contemplated for use in the practice of the present invention include those organisms in which recombinant production of heterologous proteins has been carried out. Examples of such host organisms include bacteria (e.g., *E. coli*), yeast (e.g., *Saccharomyces cerevisiae, Candida tropicalis, Hansenula polymorpha* and *P. pastoris*; see, e.g., U.S. Pat. Nos. 4,882,279, 4,837,148, 4,929,555 and 4,855,231), mammalian cells (e.g., HEK293, CHO and Ltk⁻ cells), insect cells, and the like. Presently preferred host organisms are bacteria. The most preferred bacteria is *E. coli*.

In one embodiment, nucleic acids encoding the invention AT proteins can be delivered into mammalian cells, either in vivo or in vitro using suitable viral vectors well-known in the art (e.g., retroviral vectors, adenovirus vectors, and the like). In addition, where it is desirable to limit or reduce the in vivo expression of the invention AT, the introduction of the antisense strand of the invention nucleic acid is contemplated.

Viral based systems provide the advantage of being able to introduce relatively high levels of the heterologous nucleic acid into a variety of cells. Suitable viral vectors for introducing invention AT nucleic acid encoding an AT protein into mammalian cells (e.g., vascular tissue segments) are well known in the art. These viral vectors include, for example, Herpes simplex virus vectors (e.g., Geller et al., *Science*, 241:1667–1669 (1988)), Vaccinia virus vectors (e.g., Piccini et al., *Meth. in Enzymology*, 153:545–563 (1987); Cytomegalovirus vectors (Mocarski et al., in *Viral Vectors*, Y. Gluzman and S. H. Hughes, Eds., Cold Spring Harbor Laboratory, Cold Spring Harbor, N.Y., 1988, pp. 78–84), Moloney murine leukemia virus vectors (Danos et al., *PNAS. USA*, 85:6469 (1980)), adenovirus vectors (e.g., Logan et al., *PNAS. USA*, 81:3655–3659 (1984); Jones et al., *Cell*, 17:683–689 (1979); Berkner, *Biotechniques*, 6:616–626 (1988); Cotten et al., *PNAS. USA*, 89:6094–6098 (1992); Graham et al., *Meth. Mol. Biol.*, 7:109–127 (1991)), adeno-associated virus vectors, retrovirus vectors (see, e.g., U.S. Pat. No. 4,405,712 and 4,650,764), and the like. Especially preferred viral vectors are the adenovirus and retroviral vectors.

For example, in one embodiment of the present invention, adenovirus-transferrin/polylysine-DNA (TfAdpl-DNA) vector complexes (Wagner et al., *PNAS. USA*, 89:6099–6103 (1992); Curiel et al., *Hum. Gene Therapy*, 3:147–154 (1992); Gao et al., *Hum. Gene Ther.*, 4:14–24 (1993)) are employed to transduce mammalian cells with heterologous AT nucleic acid. Any of the plasmid expression vectors described herein may be employed in a TfAdpl-DNA complex.

As used herein, "retroviral vector" refers to the well-known gene transfer plasmids that have an expression cassette encoding a heterologous gene residing between two retroviral LTRs. Retroviral vectors typically contain appropriate packaging signals that enable the retroviral vector, or RNA transcribed using the retroviral vector as a template, to be packaged into a viral virion in an appropriate packaging cell line (see, e.g., U.S. Pat. No. 4,650,764).

Suitable retroviral vectors for use herein are described, for example, in U.S. Pat. No. 5,252,479, and in WIPO publications WO 92/07573, WO 90/06997, WO 89/05345, WO 92/05266 and WO 92/14829, incorporated herein by reference, which provide a description of methods for efficiently introducing nucleic acids into human cells using such retroviral vectors. Other retroviral vectors include, for example, the mouse mammary tumor virus vectors (e.g., Shackleford et al., *PNAS, USA*, 85:9655–9659 (1988)), and the like.

In accordance with yet another embodiment of the present invention, there are provided anti-AT antibodies having specific reactivity with AT polypeptides of the present invention. Active fragments of antibodies are encompassed within the definition of "antibody". Invention antibodies can be produced by methods known in the art using invention AT polypeptides, proteins or portions thereof as antigens. For example, polyclonal and monoclonal antibodies can be produced by methods well known in the art, as described, for example, in Harlow and Lane, *Antibodies: A Laboratory Manual* (Cold Spring Harbor Laboratory (1988)), which is incorporated herein by reference. Invention AT polypeptides can be used as immunogens in generating such antibodies. Alternatively, synthetic peptides can be prepared (using commercially available synthesizers) and used as immunogens. Amino acid sequences can be analyzed by methods well known in the art to determine whether they encode hydrophobic or hydrophilic domains of the corresponding polypeptide. Altered antibodies such as chimeric, humanized, CDR-grafted or bifunctional antibodies can also be produced by methods well known in the art. Such antibodies can also be produced by hybridoma, chemical synthesis or recombinant methods described, for example, in Sambrook et al., supra., and Harlow and Lane, supra. Both anti-peptide and anti-fusion protein antibodies can be used. (see, for example, Bahouth et al., *Trends Pharmacol. Sci.* 12:338 (1991); Ausubel et al., *Current Protocols in Molecular Biology* (John Wiley and Sons, N.Y. (1989) which are incorporated herein by reference).

Antibody so produced can be used, inter alia, in diagnostic methods and systems to detect the level of AT protein present in a mammalian, preferably human, body sample, such as tissue or vascular fluid. Such antibodies can also be used for the immunoaffinity or affinity chromatography purification of the invention AT protein. In addition, methods are contemplated herein for detecting the presence of AT polypeptides either on the surface of a cell or within a cell (such as within the nucleus), which methods comprise contacting the cell with an antibody that specifically binds to AT polypeptides, under conditions permitting binding of the antibody to AT polypeptides, detecting the presence of the antibody bound to AT, and thereby detecting the presence of invention polypeptides on the surface of, or within, the cell. With respect to the detection of such polypeptides, the antibodies can be used for in vitro diagnostic or in vivo imaging methods.

Immunological procedures useful for in vitro detection of target AT polypeptides in a sample include immunoassays that employ a detectable antibody. Such immunoassays include, for example, ELISA, Pandex microfluorimetric assay, agglutination assays, flow cytometry, serum diagnostic assays and immunohistochemical staining procedures which are well known in the art. An antibody can be made detectable by various means well known in the art. For example, a detectable marker can be directly or indirectly attached to the antibody. Useful markers include, for example, radionucleotides, enzymes, fluorogens, chromogens and chemiluminescent labels.

Invention anti-AT antibodies are contemplated for use herein to modulate activity of the AT polypeptide in living animals, in humans, or in biological tissues or fluids isolated therefrom. The term "modulate" refers to a compound's ability to increase (e.g., via an agonist) or inhibit (e.g., via an antagonist) the biological activity of AT protein, such as Ac-CoA transporting activity of AT. Accordingly, compositions comprising a carrier and an amount of an antibody having specificity for AT polypeptides effective to block naturally occurring ligands or other AT-binding proteins from binding to invention AT polypeptides are contemplated herein. For example, a monoclonal antibody directed to an epitope of AT polypeptide molecules present on the surface of a cell and having an amino acid sequence substantially the same as an amino acid sequence for a cell surface epitope of an AT polypeptide including the amino acid sequence shown in SEQ ID NO:2, can be useful for this purpose.

The present invention further provides transgenic non-human mammals that are capable of expressing exogenous nucleic acids encoding AT polypeptides. As employed herein, the phrase "exogenous nucleic acid" refers to nucleic acid sequence which is not native to the host, or which is present in the host in other than its native environment (e.g., as part of a genetically engineered DNA construct). In addition to naturally occurring levels of AT, invention AT proteins can either be overexpressed, underexpressed, or expressed in an inactive mutated form (such as in the well-known knock-out transgenics) in transgenic mammals.

Also provided are transgenic non-human mammals capable of expressing nucleic acids encoding AT polypeptides so mutated as to be incapable of normal activity, i.e., do not express native AT. The present invention also provides transgenic non-human mammals having a genome comprising antisense nucleic acids complementary to nucleic acids encoding AT polypeptides, placed so as to be transcribed into antisense mRNA complementary to mRNA encoding AT polypeptides, which hybridizes to the mRNA and, thereby, reduces the translation thereof. The nucleic acid may additionally comprise an inducible promoter and/or tissue specific regulatory elements, so that expression can be induced, or restricted to specific cell types. Examples of nucleic acids are DNA or cDNA having a coding sequence substantially the same as the coding sequence shown in SEQ ID NO:1. An example of a non-human transgenic mammal is a transgenic mouse.

Animal model systems which elucidate the physiological and behavioral roles of AT polypeptides are also provided, and are produced by creating transgenic animals in which the expression of the AT polypeptide is altered using a variety of techniques. Examples of such techniques include the insertion of normal or mutant versions of nucleic acids encoding an AT polypeptide by microinjection, retroviral infection or other means well known to those skilled in the art, into appropriate fertilized embryos to produce a transgenic animal. (See, for example, Hogan et al., *Manipulating the Mouse Embryo: A Laboratory Manual* (Cold Spring Harbor Laboratory, (1986)).

Also contemplated herein, is the use of homologous recombination of mutant or normal versions of AT genes with the native gene locus in transgenic animals, to alter the regulation of expression or the structure of AT polypeptides (see, Capecchi et al., *Science,* 244:1288 (1989); Zimmer et al., *Nature,* 338:150 (1989); which are incorporated herein by reference). Homologous recombination techniques are well known in the art. Homologous recombination replaces the native (endogenous) gene with a recombinant or mutated gene to produce an animal that cannot express native (endogenous) protein but can express, for example, a mutated protein which results in altered expression of AT polypeptides.

In contrast to homologous recombination, microinjection adds genes to the host genome, without removing host genes. Microinjection can produce a transgenic animal that is capable of expressing both endogenous and exogenous AT protein. Inducible promoters can be linked to the coding region of nucleic acids to provide a means to regulate expression of the transgene. Tissue specific regulatory elements can be linked to the coding region to permit tissue-specific expression of the transgene. Transgenic animal model systems are useful for in vivo screening of compounds for identification of specific agents, i.e., agonists and antagonists, which activate or inhibit protein responses.

Invention nucleic acids, oligonucleotides (including antisense), vectors containing same, transformed host cells, polypeptides and combinations thereof, as well as antibodies of the present invention, can be used to screen compounds in vitro to determine whether a compound functions as a potential agonist or antagonist to invention AT polypeptides. These in vitro screening assays provide information regarding the function and activity of invention AT polypeptides, which can lead to the identification and design of compounds that are capable of specific interaction with one or more types of polypeptides, peptides or proteins.

In accordance with still another embodiment of the present invention, there is provided a method for identifying compounds which bind to AT polypeptides such as, for example, antibodies, binding agents, and the like. For example, the invention AT proteins may be employed in a competitive binding assay. Such an assay can accommodate the rapid screening of a large number of compounds to determine which compounds, if any, are capable of binding to AT proteins. Subsequently, more detailed assays can be carried out with those compounds found to bind, to further determine whether such compounds act as modulators, e.g., agonists or antagonists, of invention proteins.

AT is contemplated as the gene, which when defective, is responsible for abnormal neural cell differentiation and/or migration. In addition, abnormal levels of AT proteins of the present invention, such as higher or lower levels, or abnormally functioning AT proteins are contemplated as being associated with human tumors including breast cancer and cancers from ectodermal origin such as neuroblastomas and melanomas.

Thus, in another embodiment of the invention, there is provided a bioassay for identifying compounds which modulate the activity of invention AT polypeptides. According to this method, membrane bound invention AT polypeptides are contacted with Ac-CoA in the presence and in the absence of a test-compound; the activity of the AT protein is monitored subsequent to the contact with the test compound, and those substances which cause either the increase or decrease of Ac-CoA transport across the membrane having the AT proteins therein are identified as functional agents for modulating AT polypeptides.

In accordance with another embodiment of the present invention, transformed host cells (either completely-intact or semi-intact cells) that recombinantly express invention AT polypeptides can be contacted with a test compound, and the modulating effect(s) thereof can then be evaluated by comparing the AT-mediated transport of Ac-CoA (e.g., radiolabelle Ac-CoA as described in Example VI) in the presence and absence of test compound, or by comparing the response of test cells or control cells (i.e., cells that do not express AT polypeptides), to the presence of the compound.

As used herein, a compound or a signal that "modulates the activity" of invention AT polypeptides refers to a compound or a signal that alters the activity of AT polypeptides so that the activity of the invention AT polypeptide is different in the presence of the compound or signal than in the absence of the compound or signal. In particular, such compounds or signals include agonists and antagonists. An agonist encompasses a compound or a signal that activates or increases AT protein function. Alternatively, an antagonist includes a compound or signal that interferes with, inhibits or otherwise decrease AT protein function. Typically, the effect of an antagonist is observed as a blocking of agonist-induced protein activation. Antagonists include competitive and non-competitive antagonists. A competitive antagonist (or competitive blocker) interacts with or near the site specific for Ac-CoA transport. A non-competitive antagonist or blocker inactivates the function of the polypeptide by interacting with a site other than the Ac-CoA transporting region of invention AT proteins.

As understood by those of skill in the art, assay methods for identifying compounds that modulate AT activity generally require comparison to a control. One type of a "control" is a cell or culture that is treated substantially the same as the test cell or test culture exposed to the compound, with the distinction that the "control" cell or culture is not exposed to the compound. For example, a type of "control" cell or culture may be a cell or culture that is identical to the transfected cells, with the exception that the "control" cell or culture do not express native proteins. Accordingly, the response of the transfected cell to compound is compared to the response (or lack thereof) of the "control" cell or culture to the same compound under the same reaction conditions.

Accordingly, in accordance with another embodiment of the present invention, there is provided a bioassay for evaluating whether test compounds are capable of acting as agonists or antagonists for AT proteins, wherein said bioassay comprises:

(a) culturing cells containing:
DNA which expresses AT protein(s) or functional modified forms thereof,
wherein said culturing is carried out in the presence of at least one compound whose ability to modulate Ac-CoA transport activity of AT protein is sought to be determined, and thereafter (b) monitoring said cells for either an increase or decrease in the level of Ac-CoA.

Methods well-known in the art that measure incorporation of Ac-CoA, such as the transport of radiolabelled Ac-CoA into intracellular organelles, can be employed in bioassays described herein to identify agonists and antagonists of AT proteins. For example, the methods described in Example VI can be used to evaluate the AC-CoA transport activity of recombinant AT proteins or mutants and/or analogs thereof, expressed in mammalian host cells.

As used herein, "ability to modulate Ac-CoA transport activity of AT protein" refers to a compound that has the ability to either induce (agonist) or inhibit (antagonist) the Ac-CoA transport activity of AT proteins across intracellular membranes.

In another embodiment of the present invention, the bioassay for evaluating whether test compounds are capable of acting as antagonists for AT protein(s) of the invention, or functional modified forms of said AT protein(s), comprises:

(a) culturing cells containing:
DNA which expresses AT protein(s), or functional modified forms thereof,
wherein said culturing is carried out in the presence of:
increasing concentrations of at least one compound whose ability to inhibit Ac-CoA transport activity of AT protein(s) is sought to be determined, and
a fixed concentration of Ac-CoA;
and thereafter (b) monitoring in said cells the level of Ac-CoA transported into intracellular organelles as a function of the concentration of said compound, thereby indicating the ability of said compound to inhibit AT transport activity.

In step (a) of the above-described antagonist bioassay, culturing may also be carried out in the presence of:
fixed concentrations of at least one compound whose ability to inhibit Ac-CoA transport activity of AT protein(s) is sought to be determined, and
an increasing concentration of Ac-CoA.

As used herein the phrase "intracellular organelles" refers to, for example, Golgi, endoplasmic reticulum, mitochondria, and the like. Host cells contemplated for use in the bioassay(s) of the present invention include CV-1 cells, COS cells, HeLa cells, and the like. Presently, preferred host cells for carrying invention bioassays are HeLa cells as described in Example VI.

Also contemplated in yet another embodiment of the present invention, is a method for modulating the Ac-CoA transporting activity mediated by AT protein(s), said method comprising:
contacting an AT protein with an effective, modulating amount of an agonist or antagonist identified by the above-described bioassays.

Also contemplated herein is a method of treating abnormal neural cell differentiation, abnormal neural cell migration, neuroblastomas or melanomas, said method comprising administering an effective amount of a compound (agonist or antagonist) identified by the methods described herein. Such compounds are typically administered in a physiologically acceptable composition.

Accordingly, the present invention contemplates therapeutic compositions useful for practicing the therapeutic methods described herein. Therapeutic compositions of the present invention contain a physiologically compatible carrier together with an AT-1 modulating agent, or an anti-AT-1 antibody, as described herein, dissolved or dispersed therein as an active ingredient. In a preferred embodiment, the therapeutic composition is not immunogenic when administered to a mammal or human patient for therapeutic purposes.

As used herein, the terms "pharmaceutically acceptable", "physiologically acceptable" and grammatical variations thereof, as they refer to compositions, carriers, diluents and reagents, are used interchangeably and represent that the materials are capable of administration to a mammal without the production of undesirable physiological effects such as nausea, dizziness, gastric upset, and the like.

The preparation of a pharmacological composition that contains active ingredients dissolved or dispersed therein is well known in the art. Typically such compositions are prepared as injectables either as liquid solutions or suspensions; however, solid forms suitable for solution, or suspension, in liquid prior to use can also be prepared. The preparation can also be emulsified.

The active ingredient can be mixed with excipients which are pharmaceutically acceptable and compatible with the active ingredient in amounts suitable for use in the therapeutic methods described herein. Suitable excipients are, for example, water, saline, dextrose, glycerol, ethanol, or the like, as well as combinations of any two or more thereof. In addition, if desired, the composition can contain minor amounts of auxiliary substances such as wetting or emulsifying agents, pH buffering agents, and the like, which enhance the effectiveness of the active ingredient.

The therapeutic composition of the present invention can include pharmaceutically acceptable salts of the components therein. Pharmaceutically acceptable nontoxic salts include the acid addition salts (formed with the free amino groups of the polypeptide) that are formed with inorganic acids such as, for example, hydrochloric acid, hydrobromic acid, perchloric acid, nitric acid, thiocyanic acid, sulfuric acid, phosphoric acid, acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid, and the like.

Salts formed with the free carboxyl groups can also be derived from inorganic bases such as, for example, sodium hydroxide, ammonium hydroxide, potassium hydroxide, and the like; and organic bases such as mono-, di-, and tri-alkyl and -aryl amines (e.g., triethylamine, diisopropyl amine, methyl amine, dimethyl amine, and the like) and optionally substituted ethanolamines (e.g., ethanolamine, diethanolamine, and the like).

Physiologically tolerable carriers are well known in the art. Exemplary liquid carriers are sterile aqueous solutions that contain no materials in addition to the active ingredients and water, or contain a buffer such as sodium phosphate at physiological pH, physiological saline or both, such as phosphate-buffered saline. Still further, aqueous carriers can contain more than one buffer salt, as well as salts such as sodium and potassium chlorides, dextrose, polyethylene glycol and other solutes.

Liquid compositions can also contain liquid phases in addition to and to the exclusion of water. Exemplary additional liquid phases include glycerin, vegetable oils such as cottonseed oil, and water-oil emulsions.

As described herein, an "effective amount" is a predetermined amount calculated to achieve the desired therapeutic effect, e.g., to modulate the Ac-CoA transporting activity of an invention AT protein. The required dosage will vary with the particular treatment and with the duration of desired treatment; however, it is anticipated that dosages between about 10 micrograms and about 1 milligram per kilogram of body weight per day will be used for therapeutic treatment. It may be particularly advantageous to administer such compounds in depot or long-lasting form as discussed hereinafter. A therapeutically effective amount is typically an amount of an AT-modulating agent or compound identified herein that, when administered in a physiologically acceptable composition, is sufficient to achieve a plasma concentration of from about 0.1 $\mu$g/ml to about 100 $\mu$g/ml, preferably from about 1.0 $\mu$g/ml to about 50 $\mu$g/ml, more preferably at least about 2 $\mu$g/ml and usually 5 to 10 $\mu$g/ml. Therapeutic invention anti-AT antibodies can be administered in proportionately appropriate amounts in accordance with known practices in this art.

All U.S. patents and all publications mentioned herein are incorporated in their entirety by reference thereto. The invention will now be described in greater detail by reference to the following non-limiting examples.

EXAMPLES

Unless otherwise stated, the present invention was performed using standard procedures, as described, for example in Maniatis et al., *Molecular Cloning: A Laboratory Manual*, Cold Spring Harbor Laboratory Press, Cold Spring Harbor, N.Y., USA (1982); Sambrook et al., *Molecular Cloning*: A Laboratory Manual (2 ed.), Cold Spring Harbor Laboratory Press, Cold Spring Harbor, N.Y., USA (1989); Davis et al., *Basic Methods in Molecular Biology*, Elsevier Science Publishing, Inc., New York, USA (1986); or *Methods in Enzymology: Guide to Molecular Cloning Techniques* Vol.152, S. L. Berger and A. R. Kimmerl Eds., Academic Press Inc., San Diego, USA (1987).

EXAMPLE I

Description of Antibodies employed herein

Monoclonal antibody (mAb) M6703 specific for GT3 having NeuNAcα2-8NeuNAcα2-8NeuNAcα2-3Galβ1-R structure of C-series polysialogangliosides was prepared as described in Hirabayashi et al., 1988, *J. Biochem.*, 104:973–979 (incorporated herein by reference). The mAb R24 shown to react with GD3 (Pukel et al., 1982, *J. Exp. Med.*, 155:1133–1147, incorporated herein by reference), was obtained from American Type Culture Collection (ATCC #HB-8445). The mAb D1.1 which recognizes 9-O-acetylated disialogangliosides was established as described in Levine et al., 1984, *J. Neuroscience*, 4:820–831 (incorporated herein by reference), and mAb 493D4 reacting with 9-O-acetylated GT3 was provided by Dr. S. Fujita (Mitsubishi Kasei Institute of Life Sciences). Polyclonal antibodies against the synthetic N-terminal 14-amino acid peptide of the AT-1 protein (amino acids 1–14 of SEQ ID NO:2) was prepared using well-known methods.

Construction of Stably Transfected Recipient cells

This example provides methods for obtaining transfected cell lines which produce gangliosides, but not their 9-O-Ac derivatives. The purpose of this procedure is to produce cell-lines which express the gangliosides GD3 and GT3, but not their 9-O-acetylated derivatives. In order to clone a novel factor required for expression of 9-O-acetylated gangliosides, it was necessary to employ recipient cells which express a precursor ganglioside, but do not express the corresponding 9-O-acetylated ganglioside. The specific gangliosides investigated were NeuAcα2-8NeuAcα2-3Galβ1-4Glcβ1-1'Cer (hereinafter "GD3"), 9-O-Ac-GD3 (acetylated at the 9-position of the terminal neuraminic acid), NeuAcα2-8NeuAcα2-8NeuAcα2-3Galβ1-4Glcβ1-

1′Cer (hereinafter "GT3"), and 9-O-Ac-GT3 (acetylated at the 9-position of the terminal neuraminic acid).

The cell line COS-1/GD3+, which stably expresses the ganglioside GD3 but not 9-O-Ac-GD3, was prepared as previously described by Nakayama et al., (*J. Biol. Chem.*, 271:3684–3691 (1996), which is incorporated herein by reference) and HeLa/GT3+, which stably expresses the gangliosides GD3 and GT3 but not 9-O-Ac-GD3 or 9-O-Ac-GT3, was prepared as previously described (Nakayama et al., supra, 1996).

EXAMPLE II
Isolation of a cDNA Encoding AT-1

A mammalian expression vector-based cDNA library, pcDNAI-SK-MEL-28, which was constructed using poly (A)+ RNA isolated from human melanoma SK-MEL-28 cells which express 9-O-AD-GD3+ (9-O-Ac-GD3+) was purchased from Invitrogen (San Diego, Calif.) (see also U.S. Pat. No. 5,484,590, issued Jan. 16, 1996, which is incorporated herein by reference; referring to Bierhuzen and Fukuda, *Proc. Natl. Acad. Sci.. U.S.A.*, 89:9326–9330 (1992), which is incorporated herein by reference).

Approximately $1.2 \times 10^7$ COS-1/GD3+ cells were transfected with 20 μg of pcDNAI-SK-MEL-28 using lipofectamine (Life Technologies, Inc.). After sixty hours, transfected cells producing 9-O-Ac-gangliosides were stained by indirect immunofluorescence using the monoclonal antibody D1.1 (Levine et al., *J. Neuros.*, 4:820–831 (1984), which is incorporated herein by reference) which specifically binds to 9-O-Ac-GD3. Fluorescently labeled cells were isolated using fluorescence activated cell sorting using a FACStar cell sorter (Becton Dickinson).

The COS-1/GD3+ cells which stained positively for 9-O-Ac-GD3 were collected and the plasmid DNA was isolated using the Hirt procedure (Hirt, *J. Mol. Biol.*, 26:365–396 (1967), which is incorporated herein by reference). The plasmid DNA was transformed into host bacteria MC1061/P3 in the presence of ampicillin and tetracycline, and isolated from the host bacteria using well-known methods described, e.g., in Sambrook et al., (*Molecular Cloning: A Laboratory Manual*, Cold Spring Harbor, N.Y. (1989)).

The isolated pooled plasmids were subjected to sibling selection (see U.S. Pat. No. 5,484,590). Briefly, isolated plasmids were subjected to sibling selection using COS-1/GD3+ cells with sequentially smaller, active pools. The transfected cells were screened by indirect immunofluorescence microscopy using the monoclonal antibody D1.1. Positively-stained cells were collected and the plasmid DNA extracted. After subsequent rounds of sibling selection, a single plasmid, pcDNAI-AT-1, encoding a factor required for expression of 9-O-Ac-GD3 was isolated. This factor was designated AT-1 (SEQ ID NO:1).

Plasmids from selected cloned cells were isolated and the nucleotide sequence of the insert was determined in both directions. The nucleotide sequence is set forth in SEQ. ID NO: 1 (GenBank accession number D88152).

The cDNA encoding AT-1 contains an open reading frame having 1650 base pairs encoding a 549 amino acid polypeptide (SEQ ID NO:2), having a calculated molecular weight of 60,906 Da. Homology searches against protein and nucleic acid databases (GenBank, EMBL and Swiss-Prot) showed no significant homology with any known proteins, indicating that the protein encoded by AT-1 is novel. Hydropathy analysis of the AT-1 polypeptide sequence (Kyte and Doolittle (*J. Mol. Biol.*, 157:105–132 (1982)) indicated the polypeptide contained several potential transmembrane domains. (See FIG. 1). A similar analysis was performed using the programs Psort (Nakai et al., *Genomics*, 14:897–911 (1992) and Tmpred (Hofmann and Stoffel, *Biol. Chem. Hoppe-Seyler*, 347:166 (1993)). These two analyses indicated that the AT-1 polypeptide has a type IIIa membrane protein structure with 6 to 10 transmembrane domains. The AT-1 polypeptide contains a leucine zipper motif in a transmembrane domain at amino acid residues 144 through 165. It should be noted that the leucine zipper motif is often found in other transporter proteins (see, e.g., Eckhardt et al., 1996, *PNAS. USA,* 93:7572–7576; Miura et al., 1996, *J. Biochem (Tokyo)*, 120:236–241; Abeijon et al., 1996, *PNAS. USA,* 93:5963–5968).

EXAMPLE III
Expression assays characterizing the effect of AT-1 on O-acetylation of gangliosides.

COS-1/GD3+ Cells

COS-1/GD$^{3+}$ cells were transiently transfected with pcDNAI (mock transfection) or pcDNAI-AT-1. Sixty hours after transfection, the transfected cells were fixed and immunostained independently by incubation with mAb R24 (anti-GD3) or mAb D1.1 (anti-9-O-acetylated disialogangliosides), followed by rhodamine-conjugated anti-mouse IgG for mAb R24 or fluorescein isothiocyanate-conjugated anti-mouse IgM for mAb D1.1. Although there was no significant difference in R24 reactivity between mock and AT-1 transfectants, expression of 9-O-acetylated GD3 was strongly detected with mAb D1.1 in AT-1 transfectants. Only weak punctuate staining was detected in mock transfectants. These results indicate that the invention AT-1 protein mediates (affects) the 9-O-acetylation of GD3.

HeLa/GT3+ Cells

HeLa/GT3+ cells were transfected with either pcDNAI (control) or pcDNAI-AT-1, and were subsequently immunostained with the mAb 493D4, which binds to 9-O-Ac-GT3. The HeLa/GT3+/AT-1 transfected cells stained positively for 9-O-Ac-GT3, while the HeLa/GT3+/pcDNAI control cells showed no detectable staining. The staining of the HeLa/GT3+/AT-1 cells was abolished by alkali treatment (0.1N NaOH for 15 min at room temperature). These results indicate that the invention AT-1 protein mediates (affects) the 9-O-acetylation of GT3.

Establishment of Stably Transfected HeLa/GT3+/AT-1 cells

HeLa/GT3+ cells were co-transfected with pcDNA-I-AT-1 and pSV2HyB (10:1), the expression of the latter confers resistance to hygromycin B, then selected for hygromycin B resistancy. The transfected cells were screened for the presence of 9-O-Ac-GT3 by immunoflourescent staining with mAb 493D4, as discussed above. One stably transfected clone was isolated and designated HeLa/GT3+/AT-1.

Total Intracellular Ganglioside Quantification

To confirm that the cells transfected with AT-1 synthesize O-acetylated gangliosides, total gangliosides were isolated from HeLa/GT3+ cells and from their transient and stable AT-1 transfectants. It has been found that HeLa/GT3+ cells contained only simple gangliosides, GM3, GD3, GT3 and a small amount of a putative GQ3, making them ideal for examining ganglioside composition after transfection with AT-1 using thin layer chromatography.

Analytical thin-layer chromatography was carried out on precoated thin-layer chromatography plates (Kieselgel 60, Merck). The solvent system used was chloroform, methanol, 12 mM $MgCl_2$ in water (5:4:1, by volume). Gangliosides were visualized by resorcinol/HCl reagent. Isolation of gangliosides from $5 \times 10^5$ transfected cells and TLC-immunostaining was performed as described in Hirabayashi et al., *J. Biol. Chem.*, 104:973–979 (1988). Gangliosides purified from cells were applied onto a plastic plate (Polygram Sil G, Nagel, Doren, Germany) and developed under the same conditions as described above. The plate was subjected to immunostaining with mAbs followed by peroxidase-conjugated goat anti-mouse IgG antibody. The peroxidase activity was visualized with 4-chloro-1-naphthol/$H_2O_2$. Gangliosides were simultaneously analyzed after deacetylation by alkaline treatment.

The results indicate that the expression of O-Ac-GT3 and a putative O-Ac-GQ3 were strongly positive in the cells stably transfected with AT-1. Once again, no positive spots were observed when gangliosides were subjected to alkaline hydrolysis. It is important to note that HeLa/GT3+ and HeLa/GT3+/AT-1 cells contain similar amounts of total gangliosides. Also, no visible differences in the composition of neutral glycolipids and non-acetylated gangliosides have been detected using thin layer chromatographic analysis.

EXAMPLE IV
Northern Blot Analysis of AT-1 mRNA

The expression of AT-1 mRNA in various human tissues was examined by northern blot analysis. Samples of poly (A)+ RNA prepared from stably transfected HeLa cells were electrophoresed in an agarose gel containing 2.2M formaldehyde and transferred to a nylon filter (Hybond TM-N, Amersham). Hybridization with human glyceraldehyde-3-phosphate dehydrogenase (G3PDH) cDNA was performed as control experiments. These blots were hybridized with a gel-purified cDNA insert of AT-1 after labeling with [$\alpha$-$^{32}$P] dCTP by multiprime DNA labeling systems (Amersham).

Two major transcripts of AT-1 with sizes of 3.3 and 4.3 kb were detected in all tissues examined including heart, brain, placenta, lung, liver, skeletal muscle, kidney, and pancreas. Interestingly, pancreatic tissues expressed the strongest signals among the tissues examined. In the pancreas, the islets of Langerhans were shown by immunocytochemical staining to express O-acetylated sialoglycoconjugates using mAbs 493D4 and D1.1. Two transcripts of AT-1 with the size of 2.7 and 3.4 kb were expressed strongly in AT-1 transfected HeLa cells and barely detected in mock transfected HeLa cells.

EXAMPLE V
Immunohistochemical Localization of AT-1 Protein

To investigate the subcellular localization of AT-1 protein in the HeLa/GT3+/AT-1 cells, we have prepared a specific antibody to a synthetic peptide (amino acid residues 1–14 of SEQ ID NO:2 corresponding to the N-terminus of AT-1). The stably transfected cells, HeLa/GT3+/AT-1 and HeLa/GT3+/pcDNAI, were fixed, permeabilized with saponin and incubated with affinity purified rabbit anti-AT-1 antibody specific to AT-1 protein, followed by incubation with fluorescein isothiocyanate-conjugated anti-rabbit IgG.

Western blot analysis of the HeLa/GT3+/AT-1 cells with the anti-AT-1 antibody revealed a major positive band of 54 kd and a weakly reactive spot at 58 kd. Immunofluorescent analysis using affinity purified anti-AT-1 peptide indicated that this AT-1 protein is localized in the cytoplasm, including the endoplasmic reticulum, Golgi, and the mitochondria. This specific staining was not observed with preimmune IgG or in the presence of the peptide antigen.

EXAMPLE VI
Incorporation of Ac-CoA Into Semi-Intact Cells

Since it was difficult to prepare the endoplasmic reticulum or Golgi membrane fraction from cultured cells, the Ac-CoA transporter activity in cells was examined using semi-intact, permeabilized HeLa cells using the methods of Bhakdi et al. (*Infect. Immun.*, 47:52–60 (1985), which is incorporated herein by reference); Kuncan and Schlegel (*J. Cell Biol.*, 67:160–173 (1993), which is incorporated herein by reference); and Kain et al. (*J. Biol. Chem.*, 268:19640–19649 (1993), which is incorporated herein by reference). Treatment with streptolysin O (hereinafter "SLO", GIBCO BRL) generates pores in the plasma membrane of cells without any damage to intracellular membranes. This allows passage of large molecules like Ac-CoA through the plasma membrane, whose intracellular fate can then be followed.

Cultured cells were collected by trypsinization and washed successively with PBS and Hepes Calcium-free and Magnesium-free (HCMF: 0.14M NaCl-5 mM KCl-6 mM Glc-0.3 mM $Na_2HPO_4$-10 mM Hepes, pH 7.4). After treatment with activated streptolysin O (SLO, GIBCO BRL) diluted in HCMF at 28° C. for 20 min, the cells were washed and incubated with [Ac-$_{14}$C]Ac-CoA in transport buffer (TB: 25 mM Hepes-KOH-75 mM KOAc-2.5 m M MgOAc-5 mM EGTA-1.8 mM $CaCl_2$, pH 7.2) at room temperature for various periods. The reactions were quenched by addition of ice-cold TB. After the supernatant was removed by centrifugation, the pellet was washed three times with TB, solubilized with 1% SDS and the radioactivity was counted.

As shown in FIG. 2, when the semi intact cells were incubated with [Ac-$^{14}$C]Ac-CoA (35 $\mu$M), increased incorporation of radioactivity was clearly demonstrated in the AT-1 transfected cells. This effect was not seen with the mock transfectants. Upon addition of an inhibitor for the transporter, CoA (350 $\mu$M), the incorporation of radioactivity was reduced to 60% of the control. These results strongly suggest that AT-1 encodes an Ac-CoA transporter.

Although the invention has been described with reference to the examples provided above, it should be understood that various modifications can be made without departing from the spirit of the invention. Accordingly, the invention is limited only by the claims.

---

We claim:

1. An isolated nucleic acid encoding a mammalian acetyl-coenzyme A transporter (AT) protein, or a fragment thereof, wherein said nucleic acid is selected from:
   (a) DNA encoding the amino acid sequence set forth in SEQ ID NO:2, or
   (b) DNA that hybridizes to the DNA of (a) under moderately stringent conditions, wherein said DNA encodes biologically active AT, or
   (c) DNA degenerate with respect to either (a) or (b) above, wherein said DNA encodes biologically active AT, or
   (d) splice variant cDNA sequences thereof.

2. A nucleic acid according to claim 1, wherein said mammalian AT protein is selected from the group of mammals consisting of human, rat, mouse, porcine, ovine, canine or bovine.

3. A nucleic acid according to claim 1, wherein said nucleic acid hybridizes under high stringency conditions to the AT coding portion of nucleotides 388–2034 of SEQ ID NO:1.

4. A nucleic acid according to claim 1, wherein the nucleotide sequence of said nucleic acid is substantially the same as nucleotides 388–2034 set forth in SEQ ID NO:1.

5. A nucleic acid according to claim 1, wherein the nucleotide sequence of said nucleic acid encodes AT-1, and is the same as nucleotides 388–2034 set forth in SEQ ID NO:1.

6. A nucleic acid according to claim 1, wherein said nucleic acid is cDNA.

7. A vector containing the nucleic acid of claim 3.

8. Recombinant cells containing the nucleic acid of claim 1.

9. An oligonucleotide comprising at least 14 nucleotides capable of specifically hybridizing with a sequence of nucleic acids of the nucleotide sequence set forth in SEQ ID NO:1.

10. An oligonucleotide according to claim 9, wherein said oligonucleotide is labeled with a detectable marker.

11. A kit for detecting the presence of the AT cDNA sequence comprising at least one oligonucleotide according to claim 10.

12. A method for expression of AT protein, said method comprising culturing cells of claim 8 under conditions suitable for expression of said AT protein.

13. A method for identifying nucleic acids encoding a mammalian AT protein, said method comprising:

contacting a sample containing nucleic acids with an oligonucleotide according to claim 9, wherein said contacting is effected under high stringency hybridization conditions, and identifying nucleic acids which hybridize thereto.

14. A single strand DNA primer for amplification of AT nucleic acid, wherein said primer is selected from a nucleic acid sequence derived from the nucleic acid sequence set forth as SEQ ID NO: 1.

15. A bioassay for evaluating whether test compounds are capable of acting as agonists or antagonists for acetyl-coenzyme A transporter (AT) proteins characterized by being able to transport acetyl-coenzyme A (Ac-CoA) across a membrane, or functional modified forms of said AT proteins, said bioassay comprising:

(a) culturing cells containing:
DNA which expresses AT protein(s) or functional modified forms thereof,
wherein said culturing is carried out in the presence of at least one compound whose ability to modulate Ac-CoA transport activity of AT protein is sought to be determined, and thereafter (b) monitoring said cells for either an increase or decrease in the level of Ac-CoA.

16. A bioassay for evaluating whether test compounds are capable of acting as antagonists for AT protein(s) characterized by being able to transport acetyl-coenzyme A across a membrane, or functional modified forms of said AT protein (s), said bioassay comprising:

(a) culturing cells containing:
DNA which expresses AT protein(s), or functional modified forms thereof,
wherein said culturing is carried out in the presence of:
increasing concentrations of at least one compound whose ability to inhibit Ac-CoA transport activity of AT protein(s) is sought to be determined, and
a fixed concentration of Ac-CoA; and thereafter (b) monitoring in said cells the level of Ac-CoA transported into intracellular organelles as a function of the concentration of said compound, thereby indicating the ability of said compound to inhibit AT transport activity.

17. A bioassay for evaluating whether test compounds are capable of acting as antagonists for AT protein(s) characterized by being able to transport acetyl-coenzyme A across a membrane, or functional modified forms of said AT protein (s), said bioassay comprising:

(a) culturing cells containing:
DNA which expresses AT protein(s), or functional modified forms thereof,
wherein said culturing is carried out in the presence of:
fixed concentrations of at least one compound whose ability to inhibit Ac-CoA transport activity of AT protein(s) is sought to be determined, and
an increasing concentration of Ac-CoA; and thereafter (b) monitoring in said cells the level of Ac-CoA transported into intracellular organelles as a function of the concentration of said compound, thereby indicating the ability of said compound to inhibit AT transport activity.

18. A bioassay for evaluating whether test compounds are capable of acting as agonists for AT protein(s) characterized by being able to transport acetyl-coenzyme A across a membrane, or functional modified forms of said AT protein (s), said bioassay comprising:

(a) culturing cells containing:
DNA which expresses AT protein(s), or functional modified forms thereof,
wherein said culturing is carried out in the presence of:
increasing concentrations of at least one compound whose ability to increase Ac-CoA transport activity of AT protein(s) is sought to be determined, and
a fixed concentration of Ac-CoA; and thereafter (b) monitoring in said cells the level of Ac-CoA transported into intracellular organelles as a function of the concentration of said compound, thereby indicating the ability of said compound to increase AT transport activity.

19. A bioassay for evaluating whether test compounds are capable of acting as agonists for AT protein(s) characterized by being able to transport acetyl-coenzyme A across a membrane, or functional modified forms of said AT protein (s), said bioassay comprising:

(a) culturing cells containing:
DNA which expresses AT protein(s), or functional modified forms thereof,
wherein said culturing is carried out in the presence of:
fixed concentrations of at least one compound whose ability to increase Ac-CoA transport activity of AT protein(s) is sought to be determined, and
an increasing concentration of Ac-CoA; and thereafter (b) monitoring in said cells the level of Ac-CoA transported into intracellular organelles as a function of the concentration of said compound, thereby indicating the ability of said compound to increase AT transport activity.

* * * * *

UNITED STATES PATENT AND TRADEMARK OFFICE
CERTIFICATE OF CORRECTION

PATENT NO.   : 5,851,788                                                              Page 1 of 1
DATED        : December 22, 1998
INVENTOR(S)  : Fukuda et al.

It is certified that error appears in the above-identified patent and that said Letters Patent is hereby corrected as shown below:

Column 2,
Line 32, please delete "vivo" and replace therefor with -- vivo. --.

Column 5,
Line 11, please delete "coat" and replace therefor with -- that --.

Column 32,
Line 57, please delete "claim 3" and replace therefor with -- claim 1 --.

Signed and Sealed this

Twenty-fifth Day of December, 2001

Attest:

JAMES E. ROGAN
*Attesting Officer*       *Director of the United States Patent and Trademark Office*